(12) United States Patent
Carlo, III et al.

(10) Patent No.: US 12,239,306 B2
(45) Date of Patent: Mar. 4, 2025

(54) SURGICAL SYSTEM AND METHODS FOR STABILIZATION AND FIXATION OF FRACTURES, JOINTS, AND RECONSTRUCTIONS

(71) Applicant: WRIGHT MEDICAL TECHNOLOGY, INC., Memphis, TN (US)

(72) Inventors: Robert Michael Carlo, III, Lakeland, TN (US); George Matthew Awtrey, Bartlett, TN (US); Gary W. Lowery, Eads, TN (US); Joseph Ryan Woodard, Memphis, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 0 days.

(21) Appl. No.: 18/435,066

(22) Filed: Feb. 7, 2024

(65) Prior Publication Data

US 2024/0173023 A1 May 30, 2024

Related U.S. Application Data

(62) Division of application No. 17/428,674, filed as application No. PCT/US2020/026341 on Apr. 2, 2020, now Pat. No. 11,931,020.

(Continued)

(51) Int. Cl.
*A61B 17/02* (2006.01)
*A61B 17/56* (2006.01)
(Continued)

(52) U.S. Cl.
CPC .......... *A61B 17/025* (2013.01); *A61B 17/848* (2013.01); *A61B 2017/564* (2013.01);
(Continued)

(58) Field of Classification Search
CPC ................ A61B 17/025; A61B 17/848; A61B 2090/062; A61B 17/8061; A61B 2017/564; A61B 2017/681
See application file for complete search history.

(56) References Cited

U.S. PATENT DOCUMENTS 2,362,957 A 11/1944 Hackett
3,664,022 A 5/1972 Small
(Continued)

FOREIGN PATENT DOCUMENTS

EP 2326263 B1 2/2019
JP 2013502992 A 1/2013
(Continued)

OTHER PUBLICATIONS

Second Examination Report issued in connection with corresponding Australian Patent Application No. 202025610, Aug. 2, 2022, 2 pages.

(Continued)

*Primary Examiner* — Kevin T Truong
*Assistant Examiner* — Diana Jones
(74) *Attorney, Agent, or Firm* — DUANE MORRIS LLP

(57) ABSTRACT

In various embodiments, a targeting guide is disclosed. The targeting guide includes a handle defining a targeting hole and a targeting tower configured to be coupled to the handle. The targeting tower defines at least a first guide hole and a second guide hole. Each of the first and second guide holes are sized and configured to receive a respective first guide pin and second guide pin therethrough. The first and second guide pins are configured to indicate alignment of a k-wire inserted through the targeting hole defined by the handle. Methods of using a targeting guide are also disclosed.

19 Claims, 34 Drawing Sheets

Related U.S. Application Data

(60) Provisional application No. 62/829,125, filed on Apr. 4, 2019.

(51) Int. Cl.
   *A61B 17/68* (2006.01)
   *A61B 17/80* (2006.01)
   *A61B 17/84* (2006.01)
   *A61B 90/00* (2016.01)

(52) U.S. Cl.
   CPC ..... *A61B 2017/681* (2013.01); *A61B 17/8061* (2013.01); *A61B 2090/062* (2016.02)

(56) References Cited

U.S. PATENT DOCUMENTS

| | | | |
|---|---|---|---|
| 4,159,716 | A | 7/1979 | Borchers |
| 4,364,381 | A | 12/1982 | Sher et al. |
| 4,475,544 | A | 10/1984 | Reis |
| 4,570,624 | A | 2/1986 | Wu |
| 5,620,442 | A | 4/1997 | Bailey et al. |
| 5,779,709 | A | 7/1998 | Harris, Jr. et al. |
| 5,843,085 | A | 12/1998 | Graser |
| 5,893,553 | A | 4/1999 | Pinkous |
| 5,968,050 | A | 10/1999 | Torrie |
| 6,019,767 | A | 2/2000 | Howell |
| 6,589,241 | B1 | 7/2003 | Townsend et al. |
| 7,141,053 | B2 | 11/2006 | Rosa et al. |
| 7,387,296 | B2 | 6/2008 | Alberti |
| 8,080,045 | B2 | 12/2011 | Wotton, III |
| 8,231,623 | B1 | 7/2012 | Jordan |
| 8,277,459 | B2 | 10/2012 | Sand et al. |
| 8,282,645 | B2 | 10/2012 | Lawrence et al. |
| 8,313,492 | B2 | 11/2012 | Wong et al. |
| 8,764,763 | B2 | 7/2014 | Wong et al. |
| 9,622,805 | B2 | 4/2017 | Santrock et al. |
| 9,788,958 | B2 | 10/2017 | Melamed et al. |
| 9,814,473 | B2 | 11/2017 | Cummings et al. |
| 9,936,994 | B2 | 4/2018 | Smith et al. |
| 10,413,306 | B2 | 9/2019 | Russell et al. |
| 10,779,867 | B2 | 9/2020 | Penzimer et al. |
| 2002/0058944 | A1 | 5/2002 | Michelson |
| 2006/0036257 | A1 | 2/2006 | Steffensmeier |
| 2008/0009871 | A1 | 1/2008 | Orbay et al. |
| 2008/0288004 | A1 | 11/2008 | Schendel |
| 2009/0306675 | A1 | 12/2009 | Wong et al. |
| 2011/0054550 | A1 | 3/2011 | Metzinger et al. |
| 2011/0077656 | A1 | 3/2011 | Sand et al. |
| 2011/0118739 | A1 | 5/2011 | Tyber et al. |
| 2012/0016426 | A1 | 1/2012 | Robinson |
| 2012/0277745 | A1 | 11/2012 | Lizee |
| 2013/0085502 | A1 | 4/2013 | Harrold |
| 2013/0116733 | A1 | 5/2013 | Stoll, Jr. |
| 2013/0172942 | A1 | 7/2013 | Lewis et al. |
| 2014/0180348 | A1 | 6/2014 | Thoren et al. |
| 2015/0112446 | A1 | 4/2015 | Melamed et al. |
| 2015/0119944 | A1 | 4/2015 | Geldwert |
| 2016/0015426 | A1 | 1/2016 | Dayton |
| 2016/0074049 | A1 | 3/2016 | Russell et al. |
| 2016/0213384 | A1 | 7/2016 | Fallin et al. |
| 2016/0354127 | A1 | 12/2016 | Lundquist et al. |
| 2017/0014172 | A1 | 1/2017 | Fallin et al. |
| 2018/0025004 | A1 | 1/2018 | Koenig |
| 2018/0185079 | A1 | 7/2018 | Smith et al. |
| 2018/0250024 | A1 | 9/2018 | Woodard et al. |
| 2018/0280069 | A1 | 10/2018 | Barmes et al. |

FOREIGN PATENT DOCUMENTS

| | | |
|---|---|---|
| JP | 2013132519 A | 7/2013 |
| JP | 2017527430 A | 9/2017 |
| JP | 2018526127 A | 9/2018 |
| WO | 2000012035 A1 | 3/2000 |
| WO | 2009158522 A1 | 12/2009 |

OTHER PUBLICATIONS

First Office Action issued in connection with corresponding Japanese Patent Application No. 2021-557960, Oct. 4, 2022, 7 pages.

International Search Report and Written Opinion for PCT/US2020/026341 dated Jun. 24, 2020.

Bevernage, et al., "Hallux Varus: Classification and Treatment", Department of Orthopaedic Surgery, Foot Ankle Clin M. Am 14 51-65, 2009, 15 pages.

Tornier, "Futura™ Forefoot Implant Arthroplasty Products for the Surgical Treatment of Degenerative Conditions and Deformities". 2004-2008, 12 pages.

Stryker Leibinger Inc., "Lag Screw Target Bow, Leibinger Solutions for Hand Surgery", 2004, 8 pages.

Fischo, William, "A Straightforward Guide to the Lapidus Bunionectomy", https://www.hmpgloballearningnetwork.com/site/podiatry/blogged/straightforward-guide-lapidus-bunionectomy, Sep. 6, 2013, 2 pages.

Groves IV, Mack Jay, "Functional Position Joint Sectioning: Pre-Load Method for Lapidus Arthrodesis", http://www.podiatryinstitute.com/pdfs/Update_2015/2015_06, Jun. 2015, 7 pages.

Mote, et al., "First Metatarsal-Cuneiform Arthrodesis for the Treatment of First Ray Pathology: A Technical Guide", JFAS Techniques Guide, vol. 48, No. 5, Sep./Oct. 2009, pp. 593-601, 9 pages.

Fishco, William, "Making the Lapidus Easy", Chapter 14, The Podiatry Institute, 2014. 3 pages.

Dayton, Paul, "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature", The Journal of Foot and Ankle Surgery, 2013, 348-354, 8 pages.

Wolters Kluwer Health, McGlamery's Comprehensive Textbook of Foot and Ankle Surgery, Fourth Edition, 2013.

DiDomenico, et al., "Correction of Frontal Plan Rotation of Sesamoid Apparatus During the Lapidus Procedure: A Novel Approach", The Journal of Foot & Ankle Surgery, 5 pages, 2014.

Moscadini, et al., "Hallux Valgus Correction in Young Patients with Minimally Invasive Technique", The Role of Osteotomy in the Correction of Congenital and Acquired Disorders of the Skeleton, 2012, pp. 235-260, 28 pages.

Giannoudis, Peter, "Hallux Valgus Correction", Practical Procedures in Elective Orthopaedic Surgery, 2012, 12 pages.

OrthoMed, "Bone Holding Instruments" accessed via Internet on Nov. 15, 2024, https://orthomedinc.com/catalog.

Mashima, et al., "Correction of Hallux Valgus Deformity Using the Center of Rotation of Angulation Method", Journal Orthopaedic Science, 2009, 8 pages.

Wright, et al., "Intraoperative Use of the Pelvic c-clamp as an Aid In Reduction for Posterior Sacroiliac Fixation", J. Orthop Trauma, vol. 20, No. 8, Sep. 2006, 4 pages.

Klemola, et al., "First Tarsometatarsal Joint Derotational Arthrodesis-A New Operative Technique for Flexible Hallux Valgus without Touching the First Metatarsophalangeal Joint", The Journal of Foot & Ankle Surgery, 2014, 7 pages.

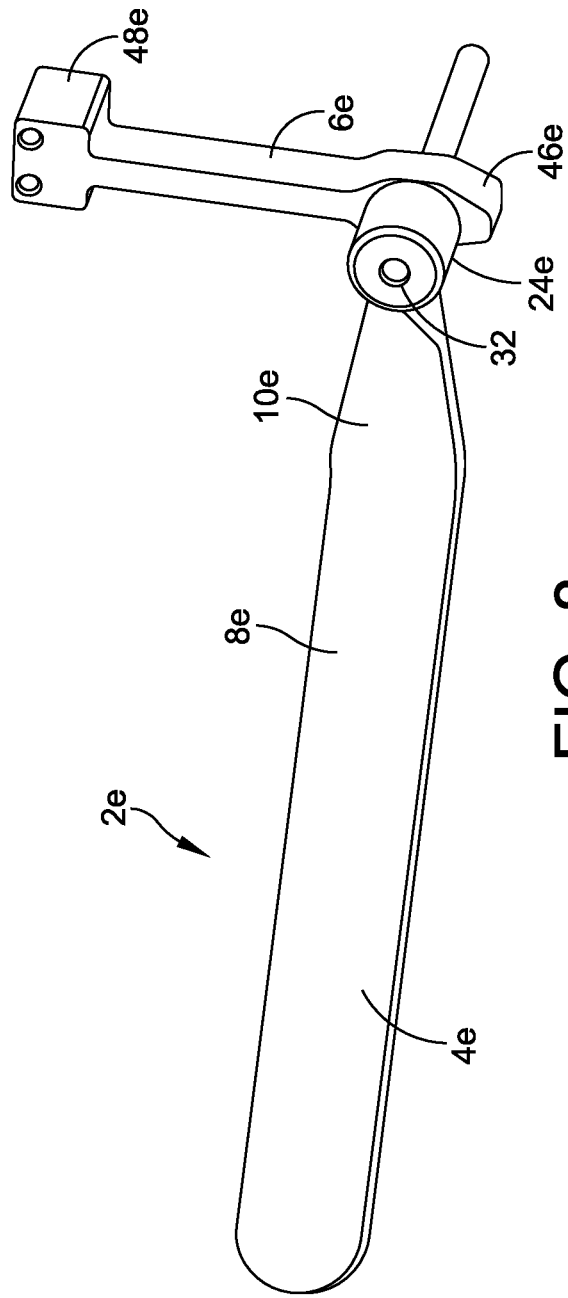
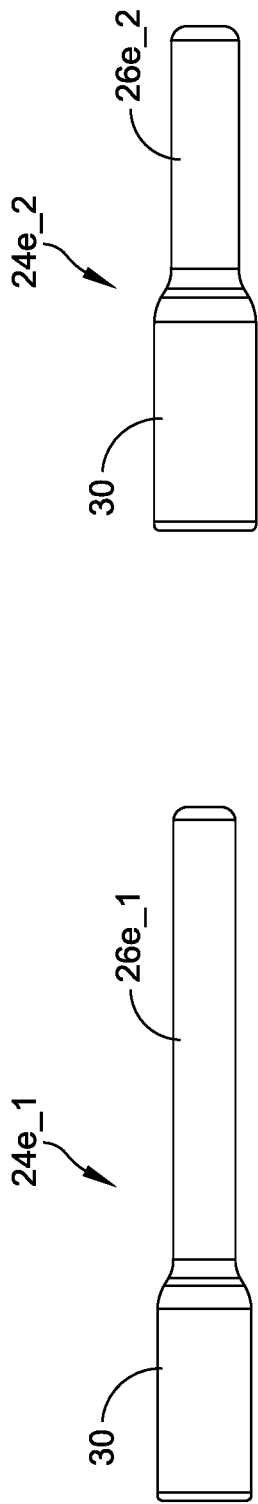

SURGICAL SYSTEM AND METHODS FOR STABILIZATION AND FIXATION OF FRACTURES, JOINTS, AND RECONSTRUCTIONS

CROSS-REFERENCE TO RELATED APPLICATIONS

This application is a divisional of U.S. patent application Ser. No. 17/428,674, filed on Aug. 5, 2021, which is a National Stage Application, filed under 35 U.S.C. 371, of International Patent Application No. PCT/US2020/026341, filed on Apr. 2, 2020, which claims the benefit of U.S. Provisional Application Ser. No. 62/829,125, filed on Apr. 4, 2019, and entitled "SURGICAL SYSTEM AND METHODS FOR STABILIZATION AND FIXATION OF FRACTURES, JOINTS, AND RECONSTRUCTIONS," the entireties of which are incorporated herein by reference.

TECHNICAL FIELD

This application relates generally to surgical systems and, more specifically, surgical systems for stabilization and fixation of bones and bone portions.

BACKGROUND

Various systems for bone fixation and targeting are known. For example, U.S. Patent Appl. Pub. No. 2018/0280069 discloses implants, guides, devices, instruments, systems and methods for fixing a joint using bone plates including an alignment guide with a first end and a second end, an alignment wire rotatably coupled to the first end of the alignment guide, and a coupling member slidingly engaging a first portion of the alignment guide near the first end. U.S. Patent Appl. Pub. No. 2018/0280069 also discloses a method of using a bone fixation system for fixation of at least two bones is also disclosed.

U.S. Pat. No. 9,545,276 discloses an internal plate fixation device for load bearing and non-load bearing fixation on a plantar side of a metatarsocuneiform joint in a Lapidus procedure. The fixation device includes a U-shaped plate having a plantar section interconnecting a pair of opposed medial legs which are bent relative to the plantar section. The plantar section is formed with a set of threaded fixation holes for receiving locking screws therein. The legs are formed with a set of threaded fixation holes for receiving locking screws therein, and a set of non-threaded fixation holes for receiving temporary K-wires and an interfragmentary compression screw which provides compression and stability at the joint.

The prior art systems have not been found adequate for targeting and fixation of fractures, joints, or reconstructions.

SUMMARY

In various embodiments, a surgical targeting guide is disclosed. The surgical targeting guide includes a handle defining a targeting hole and a targeting tower configured to be coupled to the handle. The targeting tower defines at least a first guide hole and a second guide hole. Each of the first and second guide holes is sized and configured to receive a respective first guide pin and second guide pin therethrough. The first and second guide pins are configured to indicate alignment of a k-wire inserted through the targeting hole defined by the handle.

In various embodiments, a kit is disclosed. The kit includes a targeting guide including a handle and a targeting tower coupled to the handle. The targeting tower defines a first guide hole, a second guide hole, and a targeting pin hole. Each of the first and second guide holes are sized and configured to receive a respective first guide pin and second guide pin. The kit further includes at least one first targeting pin comprising a first head and a first targeting shaft having a first length and at least one second targeting pin comprising a second head and a second targeting shaft having a second length. A circumference of the at first targeting shaft and a circumference of the second targeting shaft are equal. Each of the at least one first targeting pin and the at least one second targeting pin are configured to be slideably received within the targeting pin hole defined in the targeting tower. Each of the at least one first targeting pin and the at least one second targeting pins are configured to position a k-wire inserted through a guide hole defined therethrough parallel to and out of plane of the first and second guide pins.

In various embodiments, s method of using a targeting guide is disclosed. The method includes a step of positioning a targeting guide adjacent to a target site. The targeting guide comprising a handle defining a targeting hole and a targeting tower coupled to the handle defining at least a first guide hole and a second guide hole. A first guide pin is inserted through the first guide hole and a second guide pin is inserted through the second guide hole. The first guide pin and the second guide pin are aligned with one or more structures at the target site and with the targeting hole. A guide element is inserted through the targeting hole into at least a first bone and a second bone at the target site.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein:

FIG. 8 illustrates a surgical targeting guide including a handle and a removable targeting pin, in accordance with some embodiments.

FIG. 9 illustrates a first removable targeting pin, in accordance with some embodiments.

FIG. 10 illustrates a second removable targeting pin, in accordance with some embodiments.

DETAILED DESCRIPTION

Figure 1:
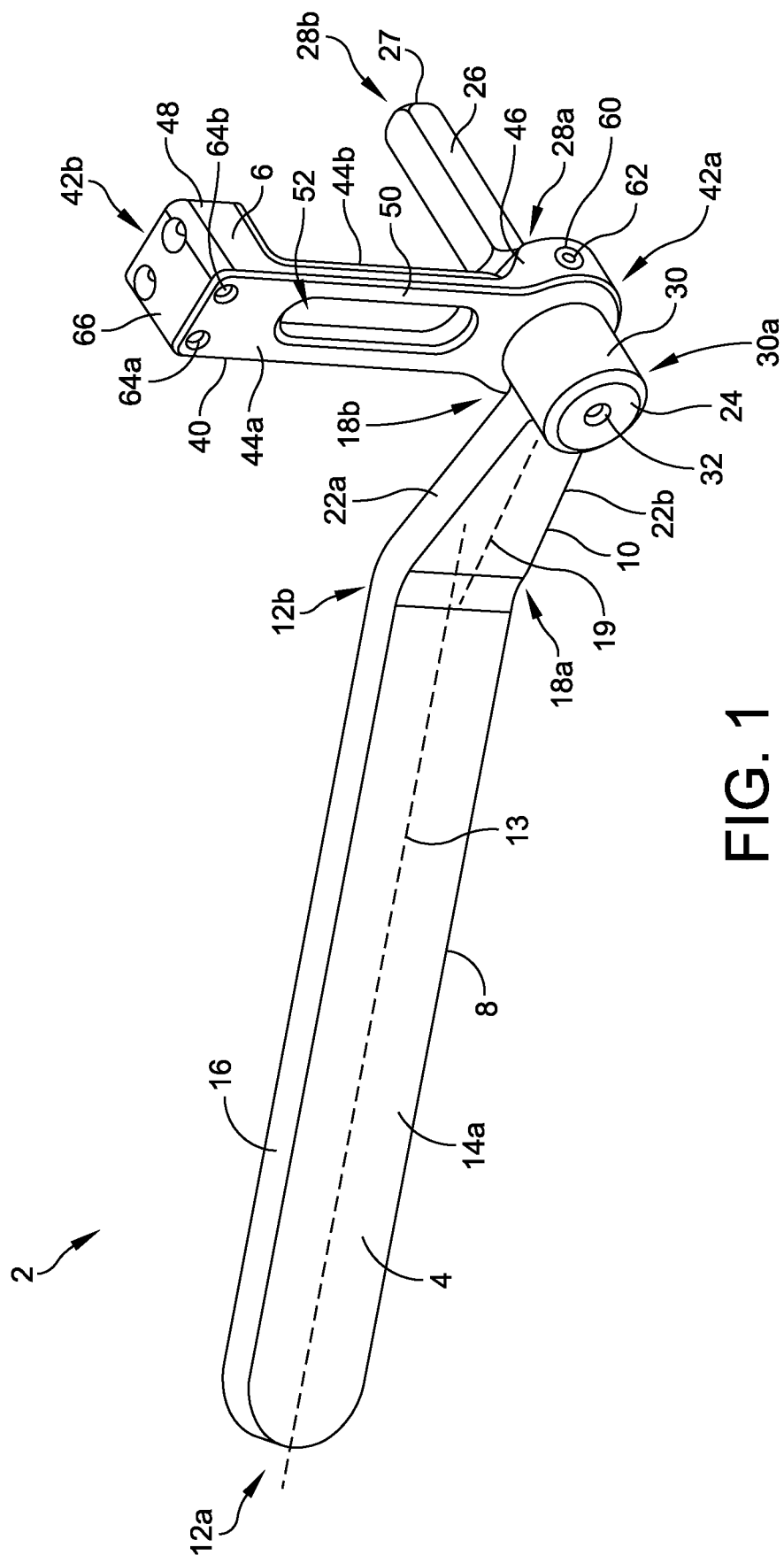
FIG. 1 illustrates a surgical targeting guide including a handle and a targeting tower, in accordance with some embodiments.

The description of the exemplary embodiments is intended to be read in connection with the accompanying drawings, which are to be considered part of the entire written description. In the description, relative terms such as "lower," "upper," "horizontal," "vertical," "proximal," "distal," "above," "below," "up," "down," "top" and "bottom," as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

As used herein, the term "substantially" denotes elements having a recited relationship (e.g., parallel, perpendicular, aligned, etc.) within acceptable manufacturing tolerances. For example, as used herein, the term "substantially parallel" is used to denote elements that are parallel or that vary from a parallel arrangement within an acceptable margin of error, such as +/−5°, although it will be recognized that greater and/or lesser deviations can exist based on manufacturing processes and/or other manufacturing requirements.

In various embodiments, surgical systems and methods for use in stabilization and fixation of fractures, revision procedures, joint fusion, and/or reconstruction of bones are disclosed, such as procedures involving bones of the feet or toes. For example, in various embodiments, the systems and method disclosed herein may be used in arthrodesis of the first metatarsal-cuneiform joint (e.g., a Lapidus fusion). Although various embodiments are disclosed herein, it will be appreciated that the systems and methods disclosed herein may be adapted for any suitable surgical procedure.

FIGS. 1-11 and 36-39 illustrate various embodiments of a surgical targeting guide 2. As illustrated in FIG. 1, in some embodiments, a surgical targeting guide 2 includes a handle 4 and a targeting tower 6. The handle 4 includes a first handle portion 8 and a second handle portion 10. The first handle portion 8 extends from a proximal end 12a to a distal end 12b substantially along a first longitudinal axis 13. The first handle portion 8 defines a substantially rectangular and/or oval body defined by a surface 14a, a second surface 14b, and a perimeter wall 16. The second handle portion 10 extends from a proximal end 18a to a distal end 18b substantially along a second longitudinal axis 19 and is defined by a first surface 20a, a second surface 20b, an upper sidewall 22a, and a lower sidewall 22b. The distal end 12b of the first handle portion 8 is coupled to the proximal end 14a of the second handle portion 10.

In some embodiments, the second handle portion 10 tapers from the proximal end 18a to the distal end 18b. For example, in the illustrated embodiment, the upper sidewall 22a is non-parallel to the second longitudinal axis 19 and the lower sidewall 22b is parallel to the second longitudinal axis 19 such that the upper sidewall 22a defines a taper from the proximal end 18a to the distal end 18b. Although embodiments are illustrated with an upper sidewall 22a defining a taper, it will be appreciated that the upper sidewall 22a and/or the lower sidewall 22b may be non-parallel with respect to the second longitudinal axis 19 such that either or both of the upper sidewall 22a and the lower sidewall 22b define a taper. In other embodiments, the second handle portion 10 is not tapered and the upper sidewall 22a and the lower sidewall 22b each extend parallel to the second longitudinal axis 19.

Figure 39:
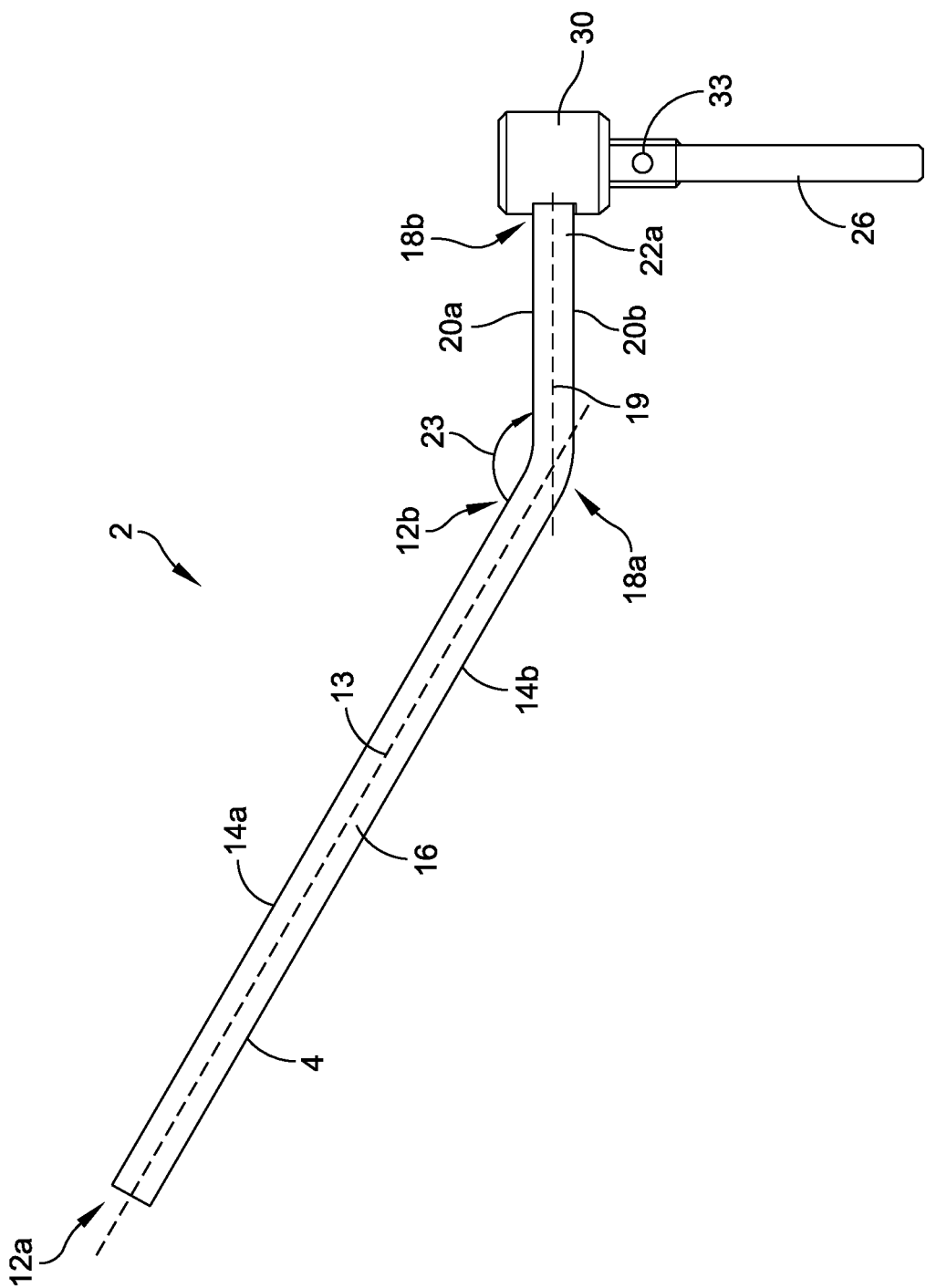
FIG. 39 illustrates a side view of the surgical targeting guide of FIG. 36, in accordance with some embodiments.

As shown in FIG. 39, in some embodiments, the second handle portion 10 is coupled to the first handle portion 8 at a non-zero angle 23 such that the second handle portion 10 extends out of a plane substantially defined by the first handle portion 8. For example, in the illustrated embodiment, the second handle portion 10 is bent (or offset) with respect to the first handle portion 8 such that the first longitudinal axis 13 and the second longitudinal axis 19 define a non-zero angle 23, such as angle between 10-80°, 15-75°, 30-60°, etc. Although various embodiments are illustrated herein, it will be appreciated that the first handle portion 8 and the second handle portion 10 may be connected at any suitable angle 23. In some embodiments, the first handle portion 8 and the second handle portion 10 are substantially parallel.

In some embodiments, the second handle portion 10 includes a targeting pin 24 configured to provide targeting of at least one k-wire. In the illustrated embodiment, the targeting pin 24 includes a targeting shaft 26 extending from a head 30. The targeting shaft 26 extends substantially from a proximal end 28a to a distal end 28b. The targeting shaft 26 is positioned at a non-zero angle with respect to the second handle portion 10. For example, in the illustrated embodiment, the targeting shaft 26 extends perpendicular to the second handle portion 10. i.e., the targeting shaft 26 defines an angle of 90° with respect to at least one of the faces 20a, 20b of the second handle portion 10. Although embodiments are illustrated including a targeting shaft 26 perpendicular to the second handle portion 10, it will be appreciated that the targeting shaft 26 may extend at any suitable non-zero angle with respect to the second handle portion 10. For example, in various embodiments, the second handle portion may extend at angle between 10-170°, 30-150°, 45-135°, 60-120°, 80-100°, etc.

The targeting shaft 26 may include a cross-section defining a shape configured to prevent rotation of a targeting tower 6 (or other element, e.g., soft tissue guard) coupled thereto. For example, in the illustrated embodiment, the targeting shaft 26 includes a rectangular cross-section that matches a rectangular opening 54 formed in the targeting tower 6 (as described in further detail below) and which prevents rotation of the targeting tower 6. Although embodiments are illustrated with a rectangular targeting shaft 26, it will be appreciated that the targeting shaft 26 may include any suitable shape complimentary to the opening 54 in the targeting tower 6 and configured to prevent rotation of the targeting tower 6. For example, in various embodiments, the targeting shaft 26 may include a cross-section defining a triangle, rectangle, pentagon, hexagon, etc. (e.g., any regular polyhedron), an irregular polyhedron, etc. In some embodiments, the targeting shaft 26 includes a circular cross-section. In such embodiments, rotation of the targeting tower 6 may be prevented by one or more anti-rotation features formed on the targeting shaft 26 and/or in the opening 54, such as, for example, one or more features extending from a first surface (e.g., the inner surface of the opening 54) and configured to interface with one or more features extending into and/or from a second surface (e.g., the targeting shaft 26), one or more fasteners inserted into one or more fastener holes, etc. Although various embodiments are discussed herein, it will be appreciated that any suitable coupling and/or anti-rotation mechanisms may be used.

In some embodiments, a head 30 is coupled to the distal end 28b of the targeting shaft 26. The head 30 may include a width (e.g., radius, diagonal, etc.) greater than the width (e.g., radius, diagonal, etc.) of a hole formed in the targeting tower 6 and configured to receive the targeting shaft 26 (as discussed in greater detail below). In some embodiments, the head defines a cylindrical shape (i.e., circular cross-section), although it will be appreciated that the head 30 may define any suitable regular and/or irregular geometric shape.

Figure 11:
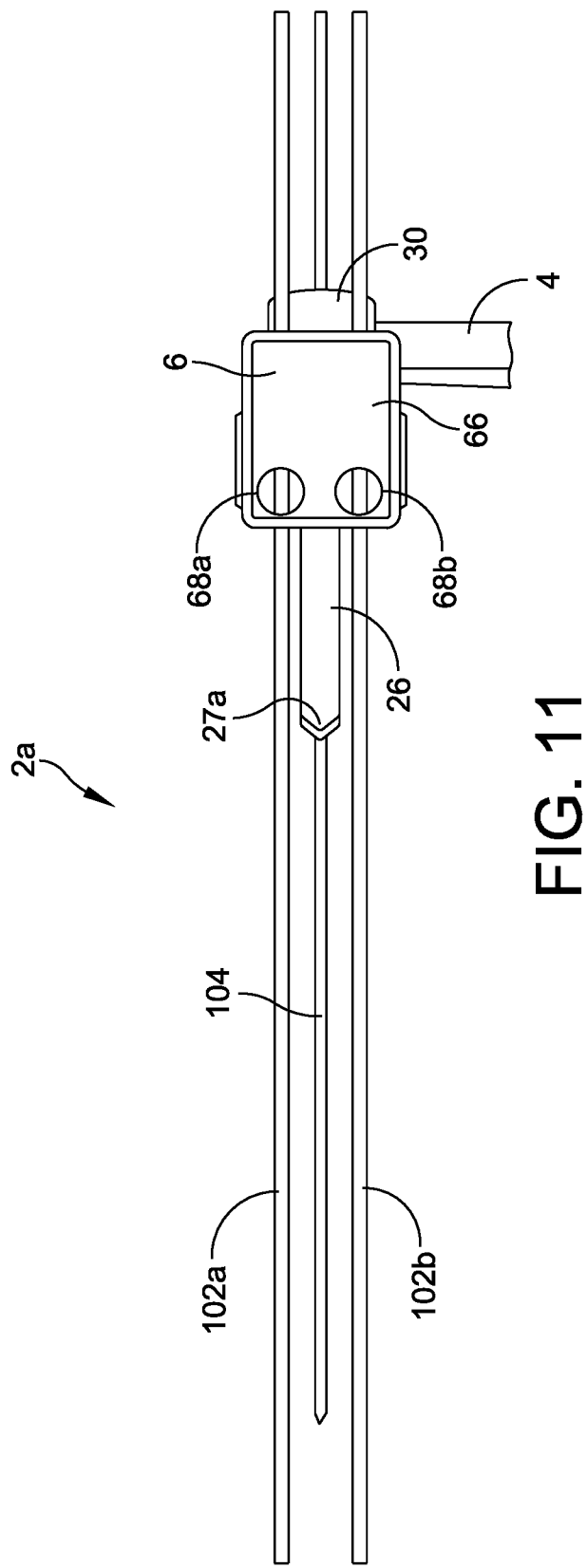
FIG. 11 illustrates the surgical targeting guide of FIG. 1 having a plurality of guide pins coupled to a targeting tower and a k-wire inserted through a targeting pin, in accordance with some embodiments.

In some embodiments, the head 30 and/or the targeting shaft 26 define a guide hole 32 extending from a proximal side 30a of the head 30 to a distal end 28b of the targeting shaft 26. The guide hole 32 may be sized and configured to receive a guide wire, such as k-wire, therein. The guide hole 32 may extend parallel to an outer surface of the head 30 and/or the targeting shaft 26 and/or may extend at an angle with respect to outer surface of the head 30 and/or the targeting shaft 26. In the illustrated embodiment, the guide hole 32 defines a concentric cylinder with respect to the head 30 and extends through a center of the targeting shaft 26. Although specific embodiments are discussed herein, it will be appreciated that the guide hole 32 may extend through any portion of the head 30 and/or the targeting shaft 26. In some embodiments, two or more guide holes may extend through the head 30 and/or the guide shaft 26. FIG. 11 illustrates a top-down view of the surgical targeting guide 2 including a k-wire 104 inserted through the guide hole 32.

Figure 6:
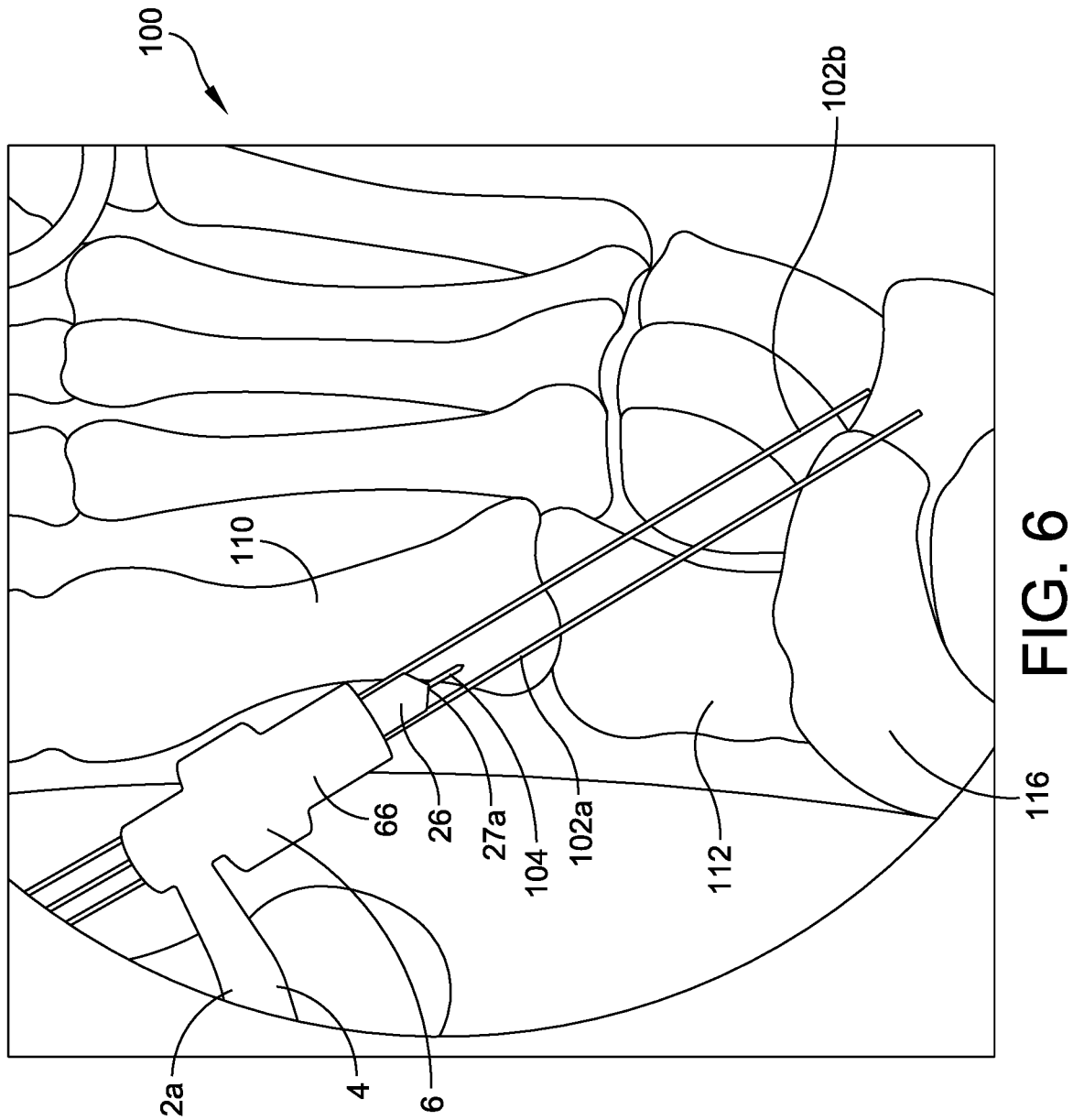
FIG. 6 illustrates a surgical site having a surgical targeting guide including handle and a plurality of guide pins positioned adjacent to a first bone, in accordance with some embodiments.
Figure 7:
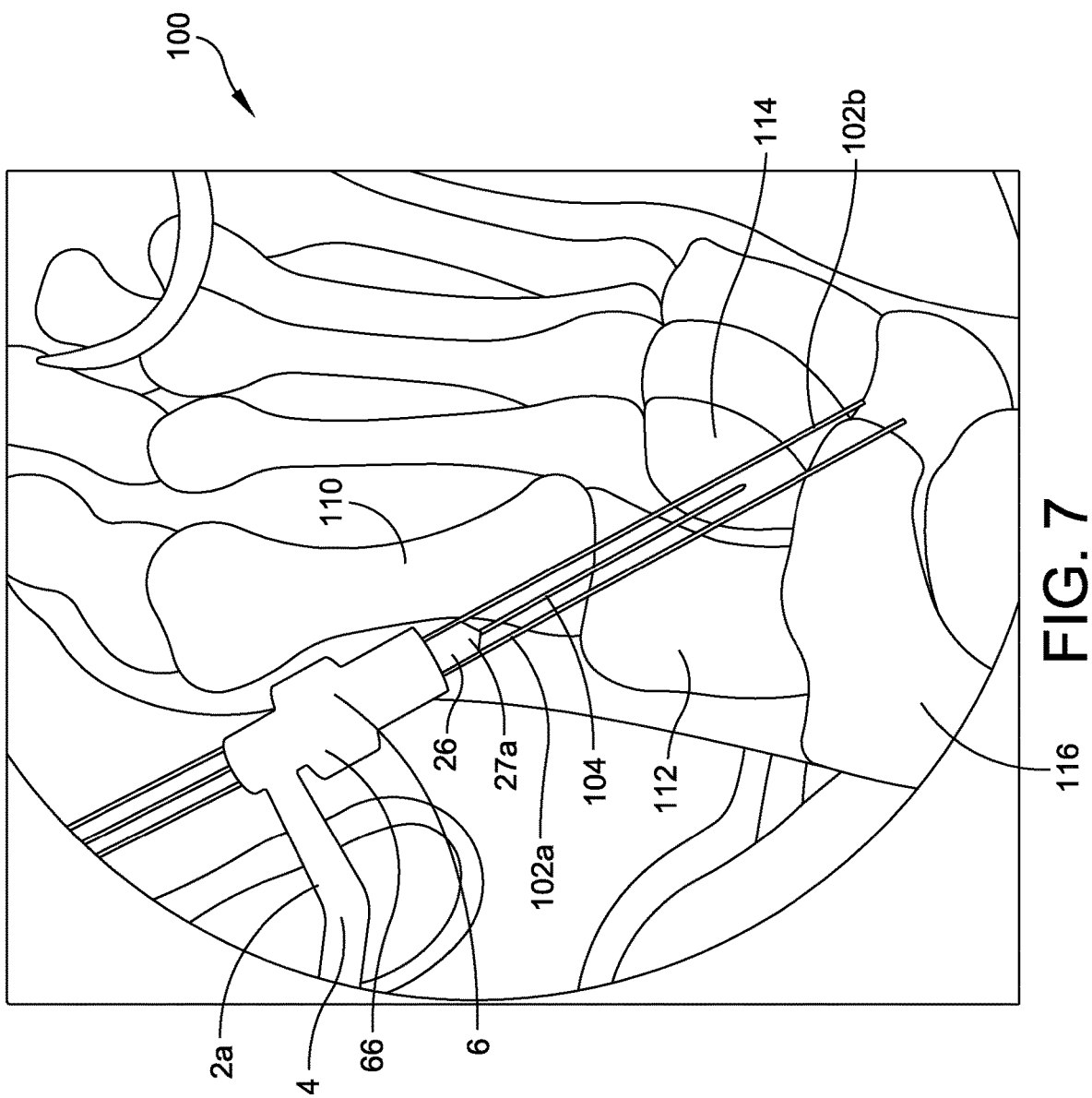
FIG. 7 illustrates the surgical site of FIG. 6 after insertion of a k-wire into a first bone using the surgical targeting guide, in accordance with some embodiments.

In some embodiments, the targeting shaft 26 includes a nose 27 positioned at a distal end 28b of the targeting shaft 26. The nose 27 may include a thickness equal to the thickness of the targeting shaft 26 (as illustrated in FIG. 1), have a tapered thickness extending from the targeting shaft 26 to a distal end 28b (as illustrated in FIGS. 6, 7, and 11 with respect to nose 27a), and/or have any other suitable shape. The targeting shaft 26 and/or the nose 27 is sized and configured to be aligned with one or more guide elements, such as guide pins or k-wires, inserted through guide holes 64a, 64b defined in the targeting tower 6 (and as described in greater detail below). For example, in some embodiments, the targeting shaft 26 and/or the nose 27 define a thickness configured to fit substantially between guide elements inserted through the guide holes 64a, 64b when viewed from above (for example, using fluoroscopy). The targeting shaft 26 and/or the nose 27 provides for alignment of the targeting shaft 26 prior to insertion of a guide element or fixation element (e.g., k-wire) through the guide hole 32 formed in the targeting shaft 26.

In some embodiments, the targeting tower 6 includes a body 40 extending from a proximal end 42a to a distal end 42b. The body 40 is defined by a proximal face 44a (facing the handle 4) and a distal face 44b. The targeting tower 6 includes a coupling portion 46, a targeting portion 48, and an extension portion 50 extending between the coupling portion 46 and the targeting portion 48. In some embodiments, and as discussed in greater detail below, the coupling portion 46 is configured to couple the targeting tower 6 to the handle 4 and the targeting portion 48 is configured to position one or more elements (e.g., guide pins, k-wires, etc.) at a predetermined positions with respect to the surgical targeting guide 2. The extension portion 50 is configured to position the targeting portion 48 at a predetermined distance (e.g., height) from the coupling portion 46. In some embodiments, the extension portion 50 includes a cutout 52 configured to reduce weight of the extension portion 50 and/or to allow visual inspection/confirmation of positioning of the surgical targeting guide 2 with respect to one or more landmarks, such as one or more anatomical structures.

Figure 37:
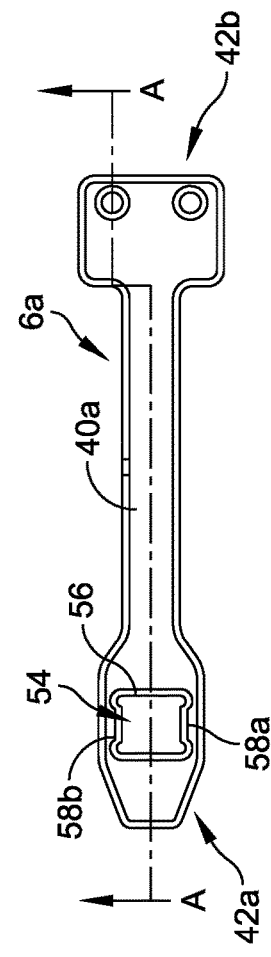
FIG. 37 illustrates a targeting tower, in accordance with some embodiments.
Figure 38:
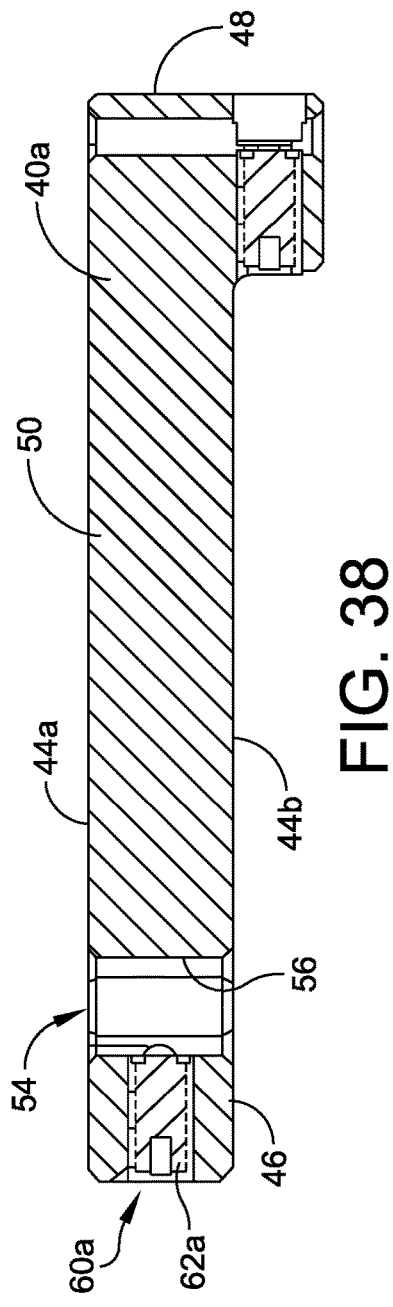
FIG. 38 illustrates a cross-section of the targeting tower of FIG. 37 taken along line A-A, in accordance with some embodiments.

In some embodiments, the coupling portion 46 of the targeting tower 6 defines an opening 54 (see FIGS. 37 and 38) sized and configured to receive the targeting shaft 26 of the handle 4 therethrough. The opening 54 includes an inner surface 56 defining a shape that is complimentary to the shape of the targeting shaft 26. For example, in the embodiment illustrated in FIG. 1, the targeting shaft 26 has a rectangular cross-section and the opening 54 defines a complimentary rectangular shape configured to receive the targeting shaft 26 therethrough. In some embodiments, the opening 54 and/or the targeting shaft 26 include one or more anti-rotation or coupling features configured to limit the angle at which the targeting tower 6 can be coupled to the handle 4 and/or to prevent rotation of the targeting tower 6 with respect to the handle 4. For example, as illustrated in FIGS. 37 and 38, in some embodiments an opening 54 formed in a targeting tower 6a includes one or more tabs or insets 58a, 58b extending from one or more sides of the inner surface 56. The tabs 58a, 58b are configured to interface with divots or other features formed in the targeting shaft 26 of the handle 4.

In some embodiments, the coupling portion 46 of the targeting tower 6 includes one or more fastener holes 60 sized and configured to receive a fastener 62 therein. The fastener 62 is configured to couple the targeting tower 6 to the targeting shaft 26. For example, in the illustrated embodiment, the fastener 62 includes a set screw configured to be tightened against an outer surface of the targeting shaft 26 and/or received within a fastener hole 33 defined in the targeting shaft 26 (see FIG. 39) after slideably coupling the targeting tower 6 to the targeting shaft 26. Further, although embodiments are illustrated including a fastener hole 60 and a fastener 62, it will be appreciated that any suitable coupling mechanism may be used to fix the position of the targeting tower 6 with respect to the targeting shaft 26. For example, in some embodiments, a detent and spring, pin, clamp, etc. may be used in place of and/or in addition to a fastener 62 to retain the targeting tower 6 in a fixed position with respect to the targeting shaft 26.

In some embodiments, the targeting portion 48 includes a targeting body 66 defining a plurality of guide holes 64a, 64b and/or viewing holes 68a, 68b. The guide holes 64a, 64b are sized and configured to receive a guide wire, guide pin, guide rail, and/or other element therethrough. In some embodiments, the viewing holes 68a, 68b are configured to allow visual inspection of guide elements inserted through the guide holes 64a, 64b. In some embodiments, the viewing holes 68a, 68b may be omitted and/or replaced with fixation holes configured to allow fixation of guide elements inserted through the guide holes 64a, 64b with respect to the targeting tower 6. For example, in some embodiments, the viewing holes 68a, 68b may be configured to receive a fixation element, such as a set screw, therein to lock or fix a guide element, such as a guide pin, in a fixed position with respect to the targeting tower 6.

In some embodiments, each of the plurality of guide holes 64a, 64b is sized and configured to receive a surgical wire and/or a guide pin therein. For example, in the illustrated embodiment, the targeting portion 48 defines a plurality of guide holes 64a, 64b extending from a first surface 44a, through a targeting body 66, and through a second surface 44b of the targeting tower 6. The plurality of guide holes 64a, 64b can include self-retaining guide holes. As shown in FIG. 11, in some embodiments, the guide holes 64a, 64b are each sized and configured to receive a respective guide pin 102a, 102b therethrough, although it will be appreciated that a k-wire and/or other radiopaque element may be used. The guide pins 102a, 102b are positioned parallel to the axis of the respective guide hole 64a, 64b. The guide pins 102a, 102b are configured to extend over anatomical structures at a predetermined distance and position with respect to the handle 4 and/or a k-wire 104 inserted through guide hole 32 formed through the targeting pin 24.

As discussed above, and as illustrated in FIGS. 6, 7, and 11, the surgical targeting guide 2 includes at least one guide hole 32 configured to provide for placement of a k-wire 104 or other guide element at a desired location when the targeting shaft 26 is aligned between guide pins 102a, 102b inserted through the guide holes 64a, 64b. In some embodiments, the surgical targeting guide 2 is used under fluoroscopy to position the guide elements 102a, 102b and/or the targeting pin 24 prior to insertion of the guide elements.

In some embodiments, the one or more guide pins 102a, 102b are inserted through the guide holes 64a, 64b to provide alignment of the targeting pin 24 with respect to one or more anatomical structures, such as, for example a first bone 110, a second bone 112, a third bone 114, and/or any other suitable number of anatomical structures. The guide pins 102a, 102b may be inserted through the guide holes 64a, 64b in the targeting tower 6 prior to insertion of a k-wire 104 through the guide hole 32 formed in the targeting pin 24. FIGS. 6-7 illustrate one embodiment of an oblique k-wire targeting a trajectory from the base of a first metatarsal 110 to an intermediate cuneiform 114. As illustrated in FIG. 6, two guide pins 102a, 102b are inserted into the guide holes 64a, 64b in the targeting tower 6. The guide pins 102a, 102b extend above the foot and do not interact with anatomical structures.

The nose 27 of the targeting pin 24 is aligned evenly between the guide pins 102a, 102b, for example, using fluoroscopy to identify the location of the guide pins 102a, 102b with respect to one or more anatomical structures and the targeting pin 24. A k-wire 104 is inserted through the guide hole 32 defined by the targeting pin 24, as shown in FIG. 7. The k-wire 104 is inserted on a trajectory that is parallel to, but out of plane, with respect to the guide pins 102a, 102b. In some embodiments, the k-wire 104 is evenly spaced between the first and second guide pins 102a, 102b and spaced apart horizontally from the plane defined by the first and second guide pins 102a, 102b. In some embodiments, guide pins 102a, 102b may provide a reference with respect to a first bone 110, a second bone 112, a third bone 114, a fourth bone 116, etc. The k-wire 104 may be inserted through the guide hole 32 and into any suitable number of bones, such as, for example, a first bone 110, a second bone 112, and a third bone 114.

Figure 2:
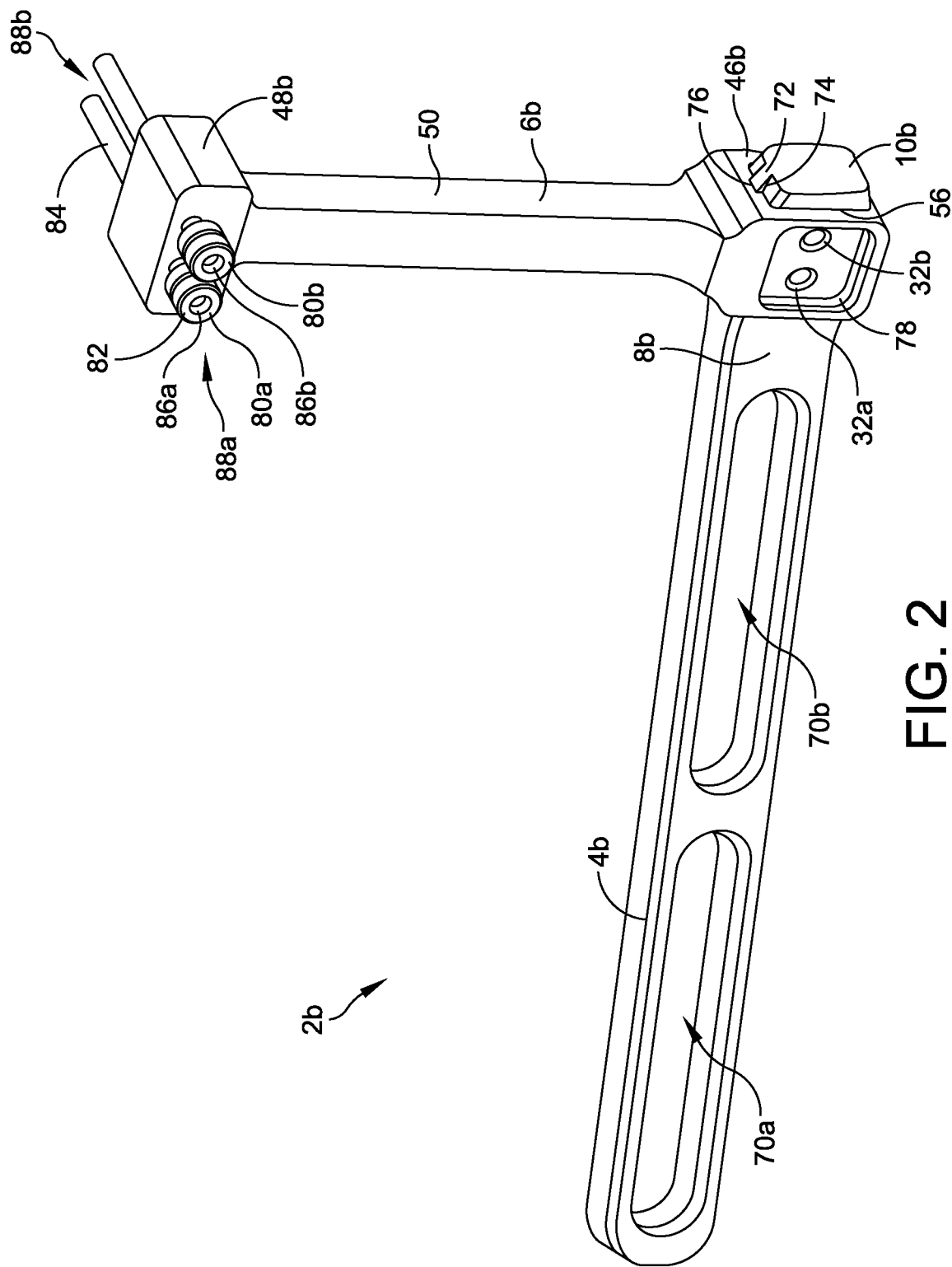
FIG. 2 illustrates a surgical targeting guide including a handle having a plurality of slots and a targeting tower coupled to the handle by a T-slot attachment, in accordance with some embodiments.

FIG. 2 illustrates a surgical targeting guide 2b, in accordance with some embodiments. The surgical targeting guide 2b is similar to the surgical targeting guides 2-2a discussed above and similar description is not repeated herein. The surgical targeting guide 2b includes a handle 4b including a plurality of cutouts 70a, 70b configured to reduce the weight of the handle 2b and/or to provide visual inspection of the alignment of the handle 4b with one or more anatomical structures.

The handle 4b includes a second handle portion 10b defining a coupling element 72 configured to fixedly couple a targeting tower 6b to the handle 4. The coupling element 72 includes a protrusion 74 (e.g., a longitudinal tab) sized and configured to interface with a coupling feature 76 (e.g., slot) formed on the surface 56 of a handle opening 54b defined in the targeting tower 6b. Although embodiments are illustrated including a T-slot coupling mechanism, it will be appreciated that the coupling element 72 and/or coupling feature 76 may include any suitable number and type of coupling mechanisms configured to couple the targeting tower 6b to the handle 4b, such as, for example, a T-slot, a dovetail, etc.

In some embodiments, a second handle portion 10b defines one or more guide holes 32a, 32b extending from a first surface 20a to a second surface 20b. The guide holes 32a, 32b are sized and configured to receive a guide element, such as a k-wire, guide pin, guide rail, etc., therethrough. The guide holes 32a, 32b may be arranged on a common longitudinal axis (as illustrated) and/or may be offset with respect to each other. In some embodiments, the guide holes 32a, 32b define parallel hole axes extending from the first surface 20a to the second surface 20b, although it will be appreciated that the guide holes 32a, 32b may define non-parallel axes through the second handle portion 10b.

In some embodiments, the targeting tower 6b defines a handle opening 54b sized and configured to receive the second handle portion 10b therethrough to couple the targeting tower 6b to the handle 4b. The targeting tower 6b may be slideably coupled to the second handle portion 10b until contacting a portion of the first handle portion 8b, which is angled with respect to the second handle portion 10b and therefore prevents further movement of the targeting tower 6b. The handle opening 54b may include one or more coupling features 76 configured to interface with coupling elements 72 formed on the second handle portion 10b to couple the targeting tower 6b to the handle 4b in a predetermined orientation and/or prevent rotation of the targeting tower 6b with respect to the handle 4b.

In some embodiments, the targeting tower 6b defines a targeting opening 78. The targeting opening 78 is sized and configured to allow access to the guide holes 32a, 32b defined in the handle 4b when the targeting tower 6b is coupled to the handle 4b. In the illustrated embodiment, the targeting opening 78 is sized similarly to the handle opening 54 but does not include a coupling feature 76. In the illustrated embodiment, the targeting opening 78 extends through the coupling portion 46b of the targeting tower 6b such that the coupling portion 46b defines a hollow square. It will be appreciated that, in some embodiments, the handle opening 54 and the targeting opening 78 may be identical such that the targeting tower 6b may be coupled to the handle 4b in two or more orientations. In some embodiments, the targeting opening 78 may be a smaller opening configured to allow access only to the guide holes 32a, 32b, although it will be appreciated that the larger, illustrated opening allows a looser alignment fit between the targeting tower 6b and the handle 4b. Further, although a single targeting opening 78 is illustrated, it will be appreciated that the targeting tower 6b may define multiple targeting openings 78, such as, for example, multiple targeting openings 78 each corresponding to a guide hole 32a, 32b formed in the handle 4b.

As illustrated in FIG. 2, in some embodiments, the guide holes 64a, 64b formed in the targeting tower 6b are sized and configured to receive guide sleeves 80a, 80b therethrough. The guide sleeves 80a, 80b may comprise parallel protuberances through which one or more guide elements, such as k-wires or guide pins, are inserted. In some embodiments, the guide sleeves 80a, 80b include a head 82 and a shaft 84 extending from the shaft 82. The head 82 includes a circumference greater than the circumference of the guide holes 64a, 64b to provide a stop to the guide sleeves 80a, 80b. Each of the guide sleeves 80a, 80b may include a wire hole 86a, 86b extending from a proximal end 88a to a distal end 88b of the guide sleeve 80a, 80b. The wire holes 82a, 82b define a hole axis parallel to a hole axis defined by a corresponding guide hole 64a, 64b in the targeting tower 6b when the guide sleeves 80a, 80b are inserted through the guide holes 64a, 64b. The wire holes 86a, 86b are sized and configured to receive a k-wire, guide pin, and/or other guide element therethrough. In some embodiments, the guide holes 64a, 64b are configured to receive one of a plurality of guide sleeves 80a, 80b therethrough. Each of the plurality of guide sleeves 80a, 80b may correspond to differently-sized surgical wires and may include a marking (e.g., color-coding, wording, etc.) corresponding to the respectively sized surgical wire. In some embodiments, the surgical targeting guide 2b provides a modular system allowing the guide sleeves 80a, 80b to be inserted to different depths, such that the surgical targeting guide 2b can be used obliquely while ensuring the guide sleeves 80a, 80b contact the bone prior to wire insertion. In some embodiments, a user (such as a surgeon) may remove and/or insert one or more guide sleeves 80a, 80b as desired.

The targeting tower 2b may be configured to accept similar, identical, and/or different guide sleeves 80a, 80b in each of the guide holes 64a, 64b. In some embodiments, pins and/or wires may be inserted directly through the holes formed in the targeting tower 6b, for example, as discussed above with respect to FIG. 1. In some embodiments, the guide sleeves 80a, 80b may be omitted and may be replaced with fixed elongated pins configured to provide similar functions as the guide sleeves 80a, 80b.

Figure 3:
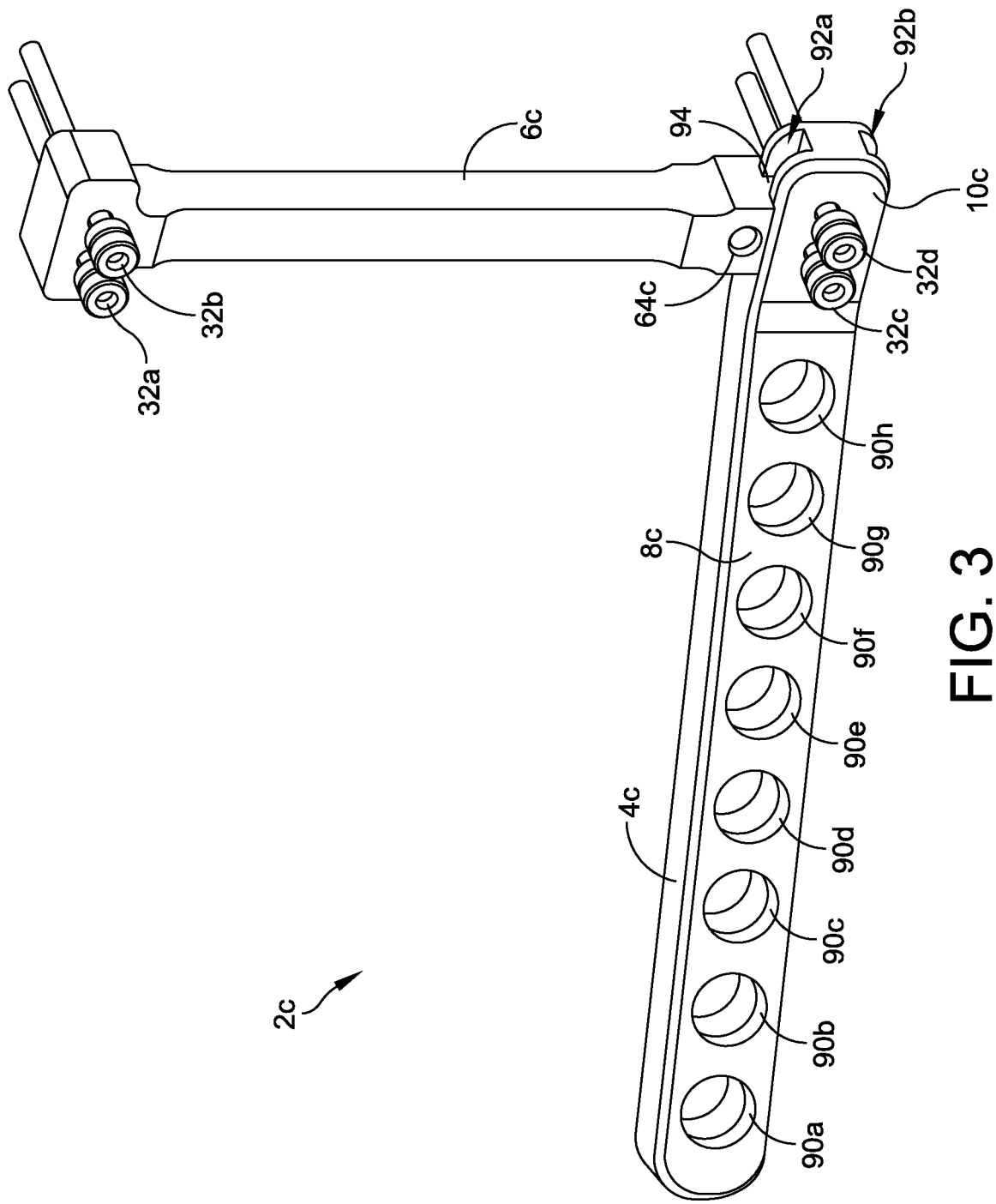
FIG. 3 illustrates a surgical targeting guide including a handle having a plurality of holes and a targeting tower coupled to the handle by a dovetail attachment, in accordance with some embodiments.

FIG. 3 illustrates a surgical targeting guide 2c, in accordance with some embodiments. The surgical targeting guide 2c is similar to the surgical targeting guides 2-2b discussed above, and similar description is not repeated herein. The surgical targeting guide 2c includes a handle 4c defining a plurality of openings 90a-90h (collectively "openings 90") through a first handle portion 8c. The openings 90 are configured to reduce the weight of the handle 4c and/or to allow visual inspection of alignment of the handle 4c with respect to one or more anatomical features.

The second handle portion 10c and the targeting tower 6c define a dovetail coupling arrangement. The second handle portion 10c defines a plurality of dovetail slots 92a, 92b sized and configured to receive a dovetail tab 94 extending from a proximal end 42a of the targeting tower 6c. The second handle portion 10c includes a first dovetail slot 92a on a first side and a second dovetail slot 92b on a second side, allowing the targeting tower 6c to be coupled to the handle 4c in at least two orientations.

In some embodiments, the targeting tower 6c defines a tool hole 64c adjacent to a proximal end 42a of the targeting tower 6c. The tool hole 64c may be sized and configured to receive a tool therein to allow coupling and/or decoupling of the targeting tower 6c to the handle 4c. In some embodiments, the tool hole 64c may function as a guide hole and may be sized and configured to receive a guide element, such as a k-wire or guide pin, therethrough.

As illustrated in FIG. 3, in some embodiments, the guide holes 32a, 32b defined by the second handle portion 10c are sized and configured to receive guide sleeves 80c, 80d therethrough. The guide sleeves 80c, 80d may be configured to receive guide elements, such as k-wires, therethrough. The guide sleeves 80c, 80d are each configured to guide insertion of a k-wire into one or more bones after aligning the surgical targeting guide 2c with one or more anatomical features using guide pins 102a, 102b inserted through the guide sleeves 80a, 80b.

Figure 4:
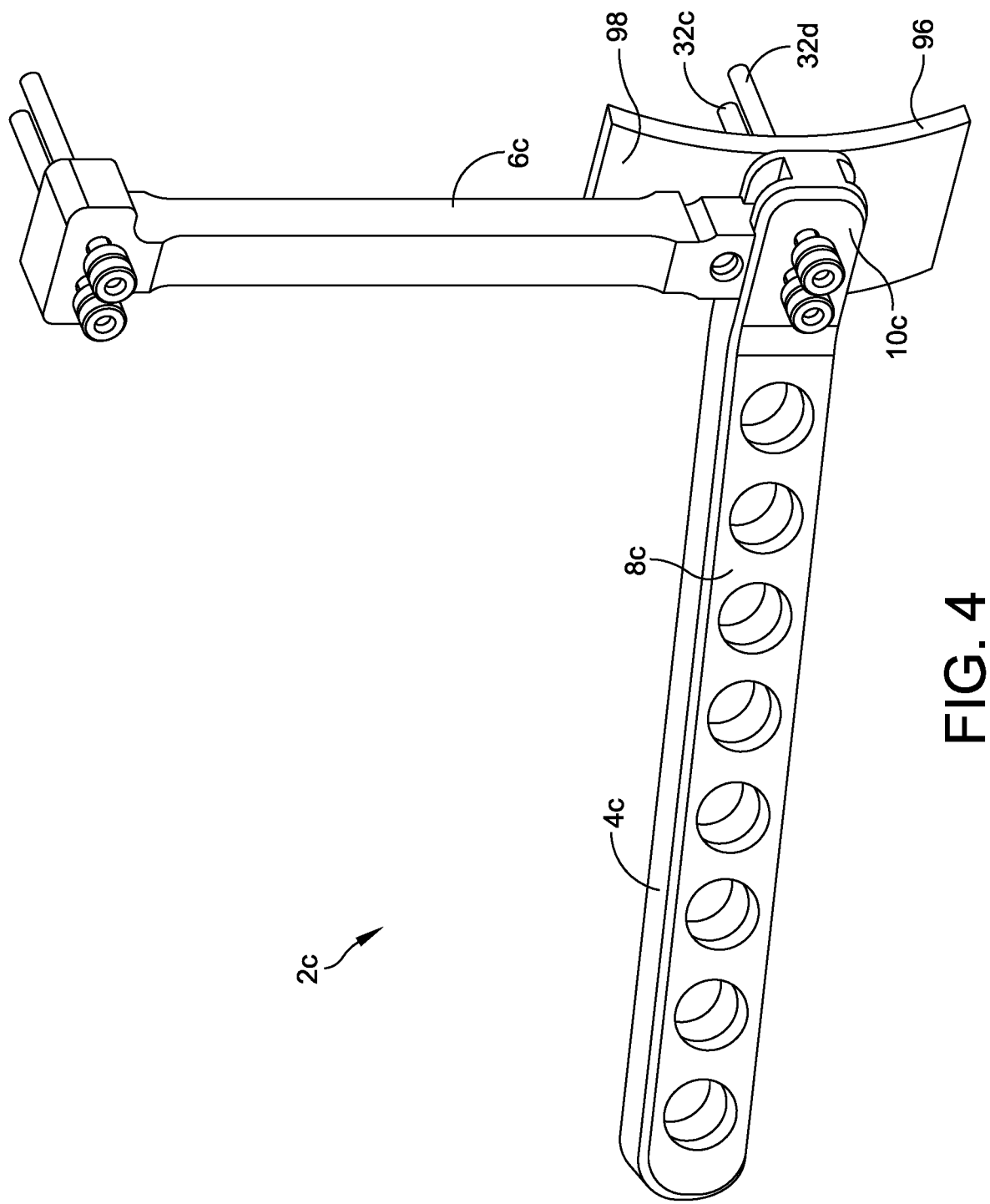
FIG. 4 illustrates the surgical targeting guide of FIG. 3 having a contoured soft tissue guard coupled thereto, in accordance with some embodiments.

As illustrated in FIG. 4, in some embodiments, a contoured soft tissue guard 96 may be coupled to a surgical targeting guide, such as the surgical targeting guide 2c. The contoured soft tissue guard 96 includes a body 98 defining a one or more openings. The openings may be sized and configured to receive a coupling element, such as a guide sleeve 80c, 80d, therethrough. The body 98 of the soft tissue guard 96 is configured to interface with soft tissue at a surgical site to improve stability of the surgical targeting guide 2c, reduce angulation of the handle 4c with respect to a target site, and/or provide additional functionality, such as alignment, soft tissue protection, etc. The soft tissue guard can be configured for use in conjunction with the targeting tower 6c or for use without the targeting tower 6c.

Figure 5:
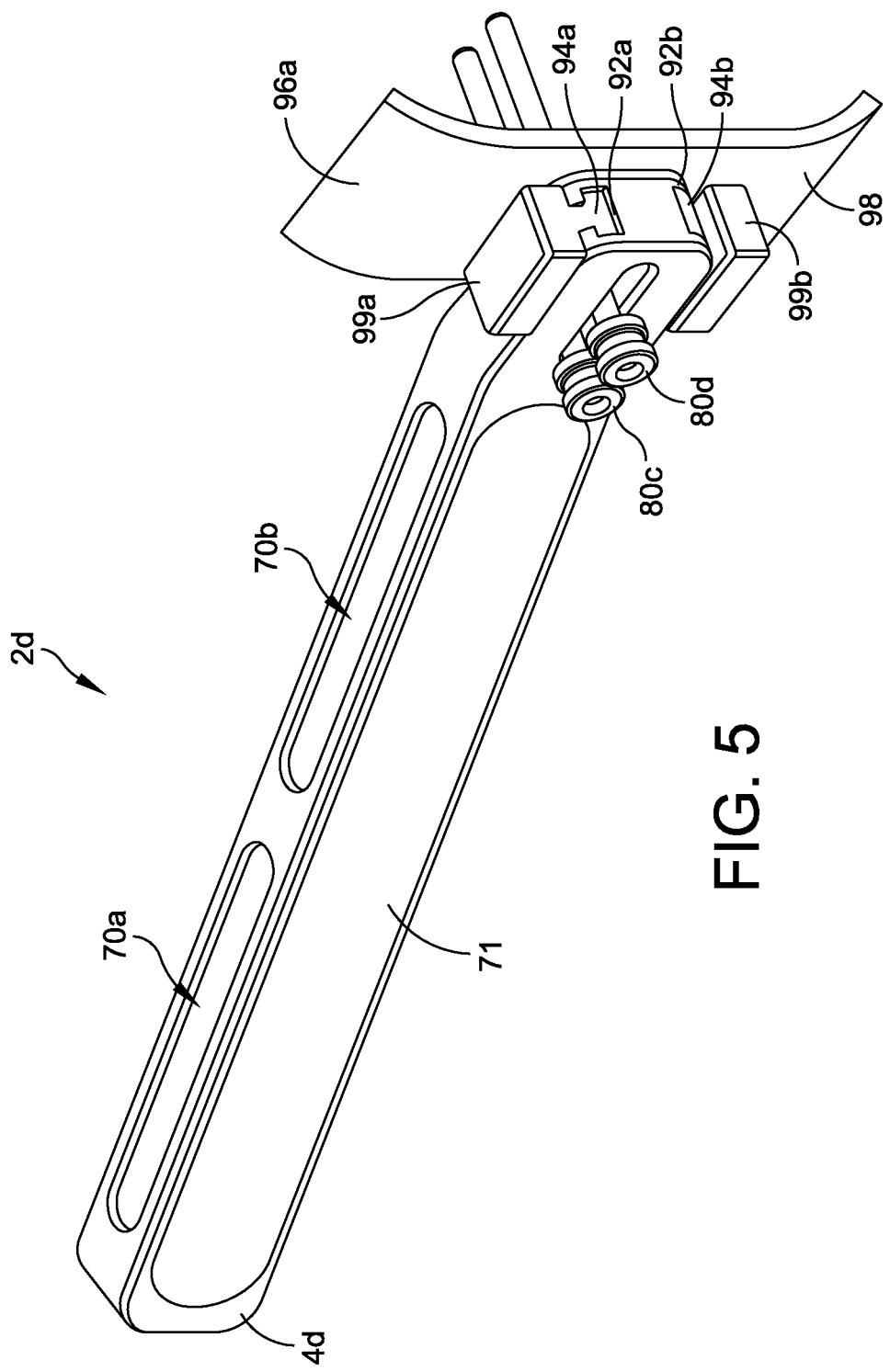
FIG. 5 illustrates a surgical targeting guide including a handle having a tissue guard coupled thereto, in accordance with some embodiments.

FIG. 5 illustrates an embodiment of a surgical targeting guide 2d, in accordance with some embodiments. The surgical targeting guide 2d is similar to the surgical targeting guide 2c discussed above, and similar description is not repeated herein. The surgical targeting guide 2d includes a handle 4d having a second handle portion 10d defining a slot 33 sized and configured to receive one or more guide sleeves 80c, 80d therethrough. The slot 33 is configured to allow the guide sleeves 80c, 80d to be positioned through the second handle portion 10d at variable longitudinal positions. In some embodiments, the variable longitudinal position may be fixed by a friction fit with the head 82 of a respective guide sleeve 80c, 80d against the surface of the second handle portion 10d and/or maintained by a separate element, such as, for example, a soft tissue guard 96a coupled to the second handle portion 10d (as discussed in greater detail below). In some embodiments, the handle 4d includes a plurality of cutouts 70a, 70b and a divot 71 configured to reduce the weight of the handle 4d and/or facilitate gripping of the handle 4d.

As illustrated in FIG. 5, a soft tissue guard 96a may be coupled to a handle 4d of a surgical targeting guide 2d independent of a targeting tower. The surgical targeting guide 2d may include one or more holes sized and configured to receive a guide sleeve 80a, 80b therethrough. In some embodiments, one or more support elements 99a, 99b may be configured to couple to the second handle portion 10d to provide support to the soft tissue guard 96a and/or the handle 4d. The support elements 99a, 99b may be integrally formed with the soft tissue guard 96a and the soft tissue guard 96a may be coupled to the handle 4d by slideably interfacing longitudinal tabs 94a, 94b formed on the support elements 99a, 99b with slots 92a, 92b, such as T-slots, formed in the handle 4d. In other embodiments, the support elements 99a, 99b may be separate elements that can be independently coupled to the handle 4d.

FIG. 8 illustrates a surgical targeting guide 2e including a removable targeting pin 24e, in accordance with some embodiments. The surgical targeting guide 2e is similar to the surgical targeting guides 2-2d discussed above, and similar description is not repeated herein. The surgical targeting guide 2e includes a handle 4e having a targeting tower 6e fixedly coupled to and/or formed integrally with a distal end 12b. The targeting tower 6e includes an opening (similar to the opening 54 illustrated in FIG. 37) sized and configured to receive a targeting pin 24e therethrough. It will be appreciated that rotation of the targeting pin 24e within the targeting tower 6e does not change the targeting trajectory of the guide hole 32 and therefore anti-rotation features may be omitted from the opening in the targeting tower 6e and/or on the targeting shaft 26e.

In some embodiments, the targeting tower 6e is configured to receive one of a plurality of targeting pins therethrough. For example, FIGS. 9 and 10 illustrate two embodiments of targeting pins 24e_1, 24e_2 that may be inserted through the opening defined in the targeting tower 6e. Each of the targeting pins 24e_1, 24e_2 includes a head 30 and a targeting shaft 26e_1, 26e_2. The length of each of the targeting shafts 26e_1, 26e_2 may correspond to different anatomical lengths and/or positions and may be selected by a user, e.g., a surgeon, during an operation to match the anatomy of a specific patient. In some embodiments, the diameter of each of the targeting shafts 26e_1, 26e_2 are equal such that any of the targeting pins 24e_1, 24e_2 may be coupled to the targeting tower 6e through any of the respective guide holes 64a, 64b.

Figure 13:
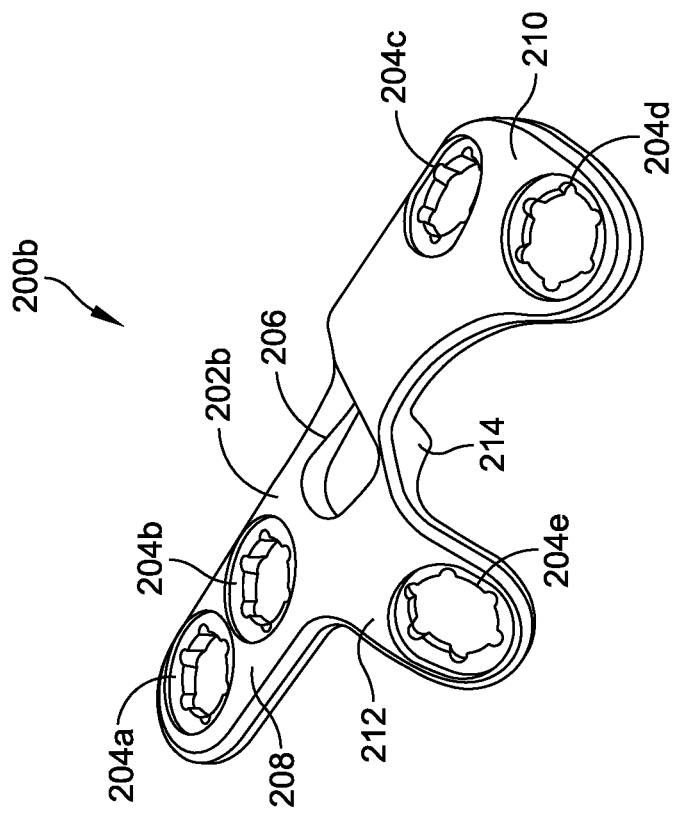
FIG. 13 illustrates a bone plate including an offset plate portion and having a plurality of variable angle fastener holes and a compression slot, in accordance with some embodiments.
Figure 12:
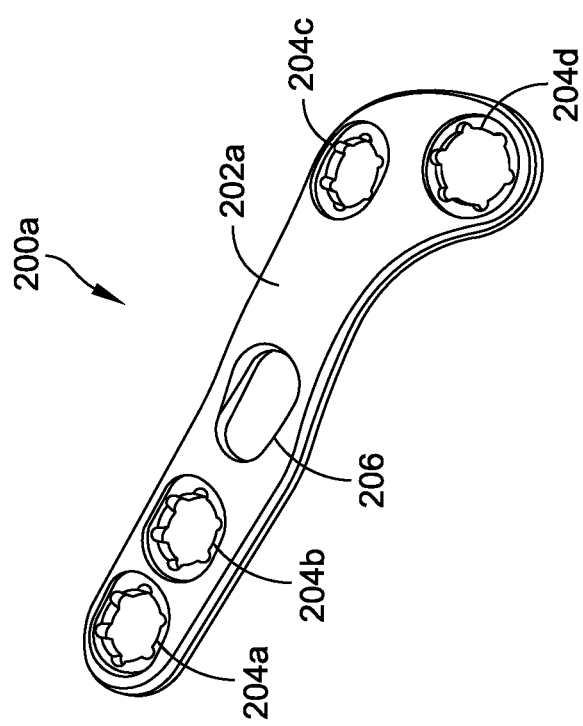
FIG. 12 illustrate a bone plate including a plurality of variable angle fastener holes and a compression slot, in accordance with some embodiments.

FIGS. 12-17 illustrate a set of surgical tools configured to be used in one or more surgical techniques utilizing the surgical targeting guides described above, such as, for example, a lapidus surgical technique. FIGS. 12 and 13 illustrate bone plates 200a, 200b. Bone plate 200a includes a body 202a defining a plurality of variable angle fastener holes 204a-204d and at least one compression slot 206. The bone plate 200b includes a body 202b defining having one or more contours or curves configured to match a predetermined anatomical structure. Similar to bone plate 200a, bone plate 200b includes a plurality of variable angle fastener holes 204a-204e and at least one compression slot 206. Bone plate 200b further includes a first body portion 208, a second body portion 210, and a third body portion 212. The second body portion 210 is coupled to the first body portion 208 by an offset portion 214 that positions the second body portion 210 in a plane above or below the first body portion 208. The third body portion 212 extends from the first body portion 208 perpendicular to an axis of the first and second body portions 208, 210. The third body portion 212 defines at least one of the variable angle fastener holes 202e. Although specific embodiments are illustrated, it will be appreciated that a set of surgical tools for use in one more surgical techniques, such as, for example, various bone plates available from Wright Medical Technology under the brand name Ortholoc™ 2.

Figure 14:
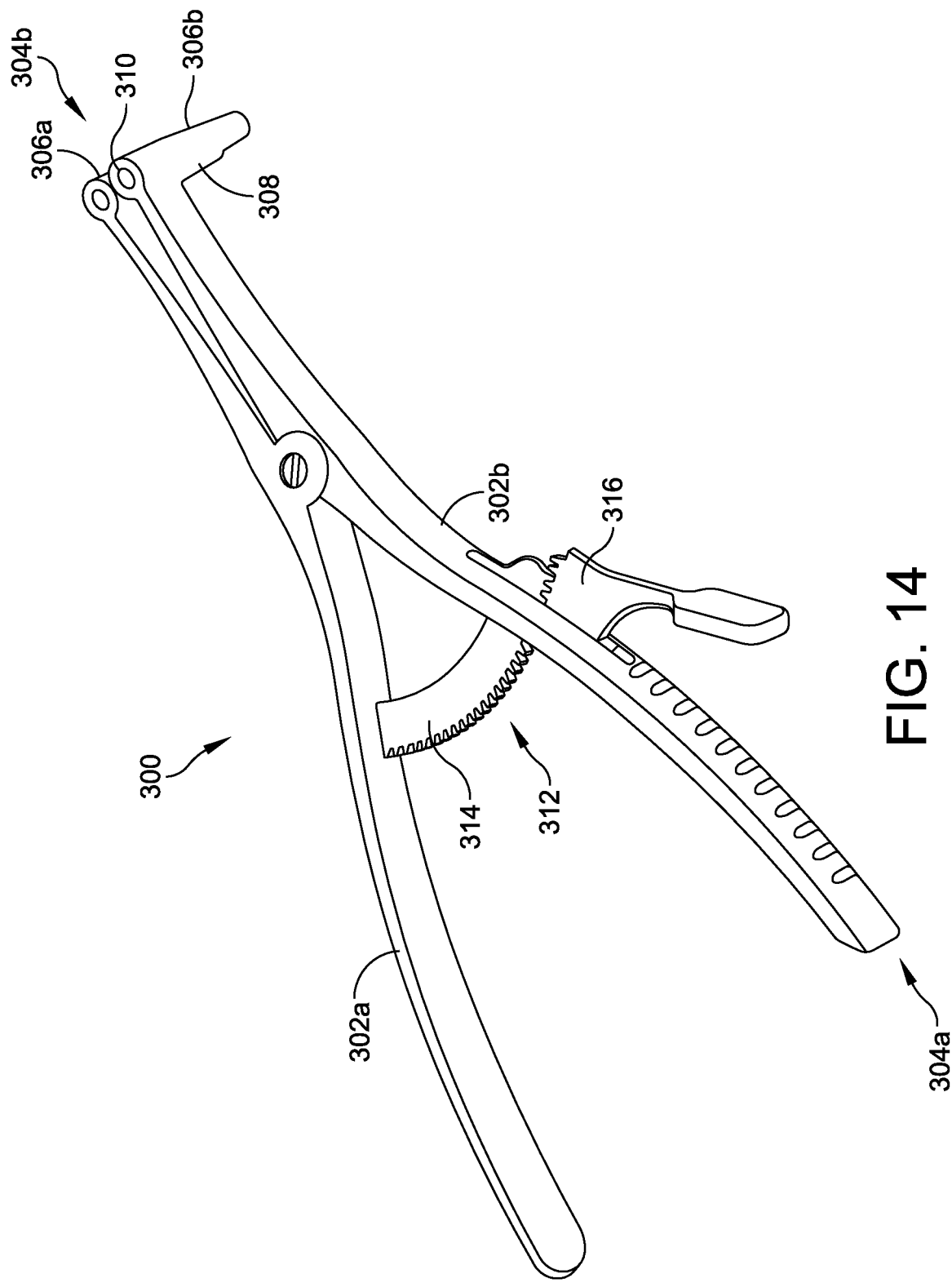
FIG. 14 illustrates a distractor configured to be coupled to one or more pins inserted into at least a first bone, in accordance with some embodiments.

FIG. 14 illustrates a surgical distractor 300, in accordance with some embodiments. The surgical distractor 300 includes a first handle 302a and a second handle 302b extending from a proximal end 304a to a distal end 304b and coupled in a scissor-like arrangement. Each of the first handle 302a and the second handle 302b include a coupling head 306a, 306b at a distal end 304b thereof. The coupling heads 306a, 306b each include a body 308 defining an opening 310 extending therethrough sized and configured to receive a guide element, such as a k-wire, pin, etc., therethrough.

In some embodiments, the surgical distractor 300 includes a ratcheting assembly 312 configured to provide ratcheting separation of the coupling heads 306a, 306b. The ratcheting assembly 312 includes a first ratcheting gear 314 coupled to the first handle 304a and a second ratcheting gear 316 coupled to the second handle 304b. As discussed in greater detail below, the surgical distractor 300 is configured to provide distraction of a first bone and a second bone during a surgical procedure.

Figure 15:
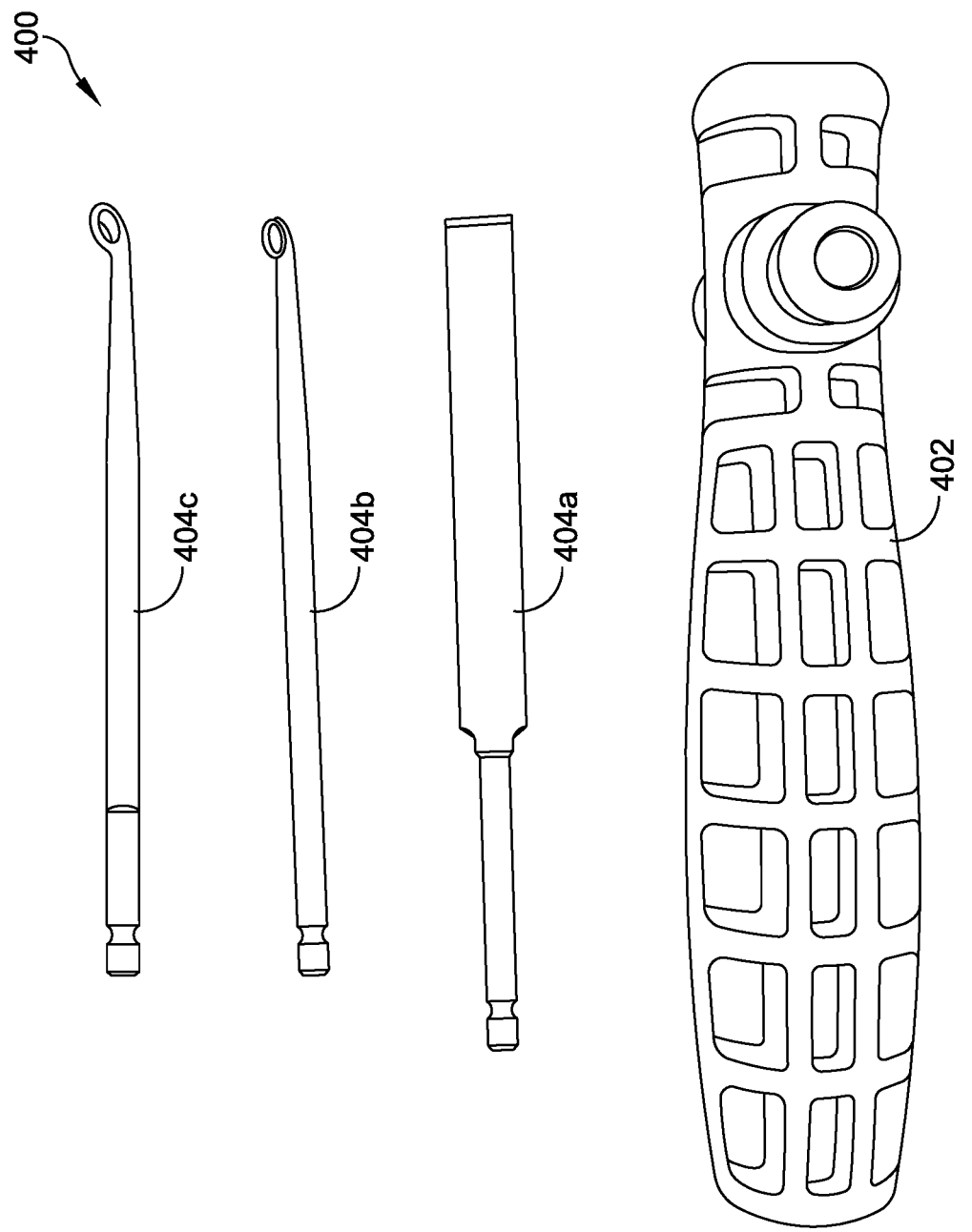
FIG. 15 illustrates various elements of a joint preparation instrument, in accordance with some embodiments.

FIG. 15 illustrates various elements of a joint preparation instrument 400, in accordance with various embodiments. The joint preparation instrument 400 includes a handle 402 configured to releasably and selectively couple to various head elements 404a-404c. Each of the head elements 404a-404c are configured to perform joint preparation, such as, for example, a curette 404a configured to remove cartilage within a joint space and/or osteotomes 404b, 404c configured to provide feathering of a bony surfaces within a joint. Although specific embodiments are illustrated herein, it will be appreciated that any suitable head element may be coupled to the handle 402 to allow preparation of a surgical site during a surgical procedure.

Figure 16:
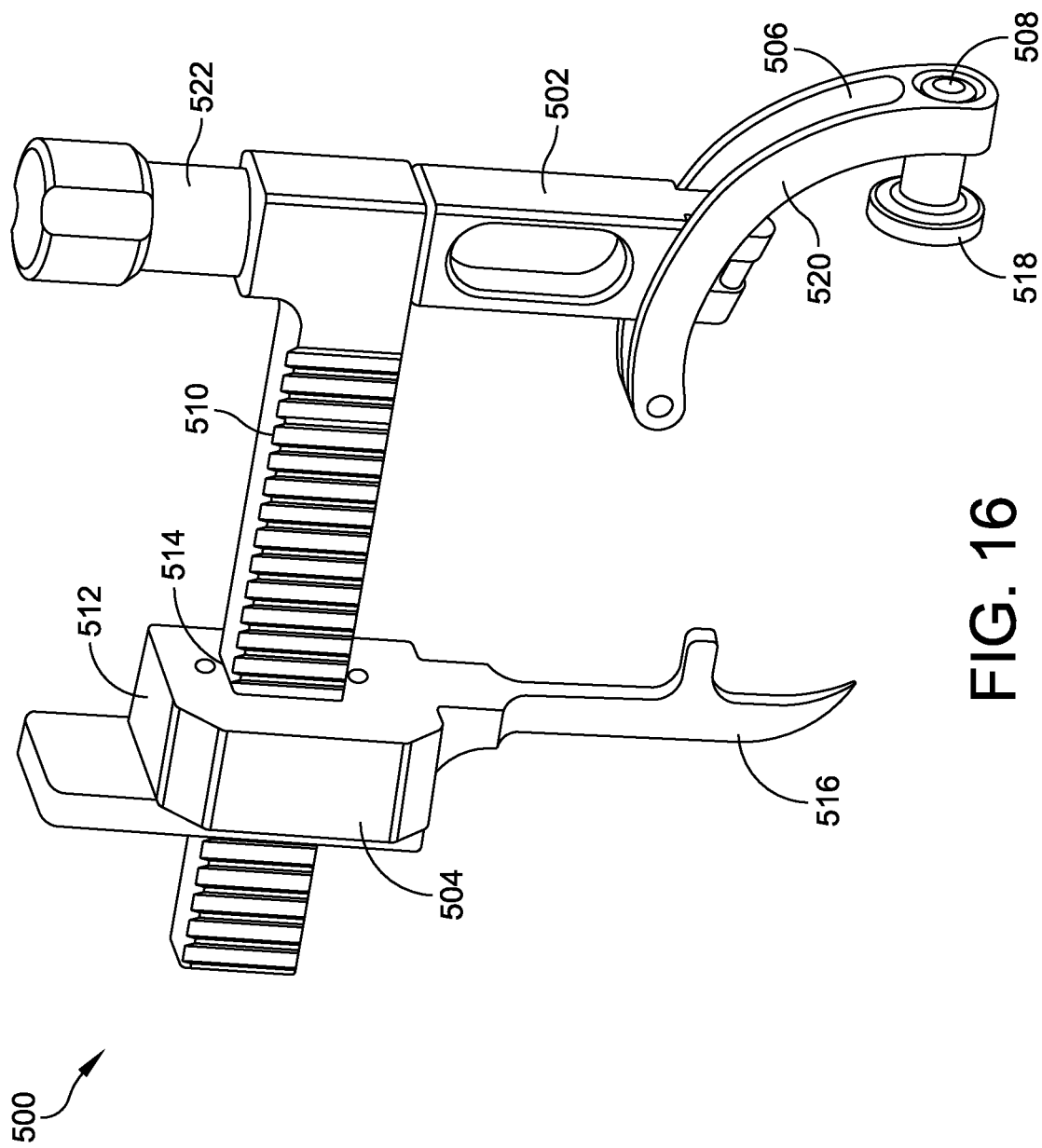
FIG. 16 illustrates a clamp configured to reduce an intrametatarsal (IM) angle between a first bone and a second bone, in accordance with some embodiments.

FIG. 16 illustrates a clamp 500 configured to releasably couple a first bone to a second bone, in accordance with some embodiments. The bone clamp 500 includes a ratcheting barrel portion 502 and a hook portion 504. The ratcheting barrel portion 502 includes a barrel head 506 configured to interface with a first bone. The barrel head 506 includes a contact head 518 defining a guide hole 508 sized and configured to receive a guide element, such a k-wire, therethrough. In some embodiments, the ratcheting barrel portion 502 includes an angle rotation element 520 configured to provide rotation of the barrel head 506 with respect to a ratcheting element 510. The hook portion 504 includes a body 512 defining a ratcheting opening 514 sized and configured to receive the ratcheting element 510 therethrough. A hook 516 extends from the body 512 and is sized and configured to interface with a second bone. As discussed below, in operation, the bone clamp 500 is configured to reduce the distance between two anatomical structures (e.g., bones) until a desired angle is achieved and/or to perform a de-rotation procedure of one or more anatomical structures.

Figure 17:
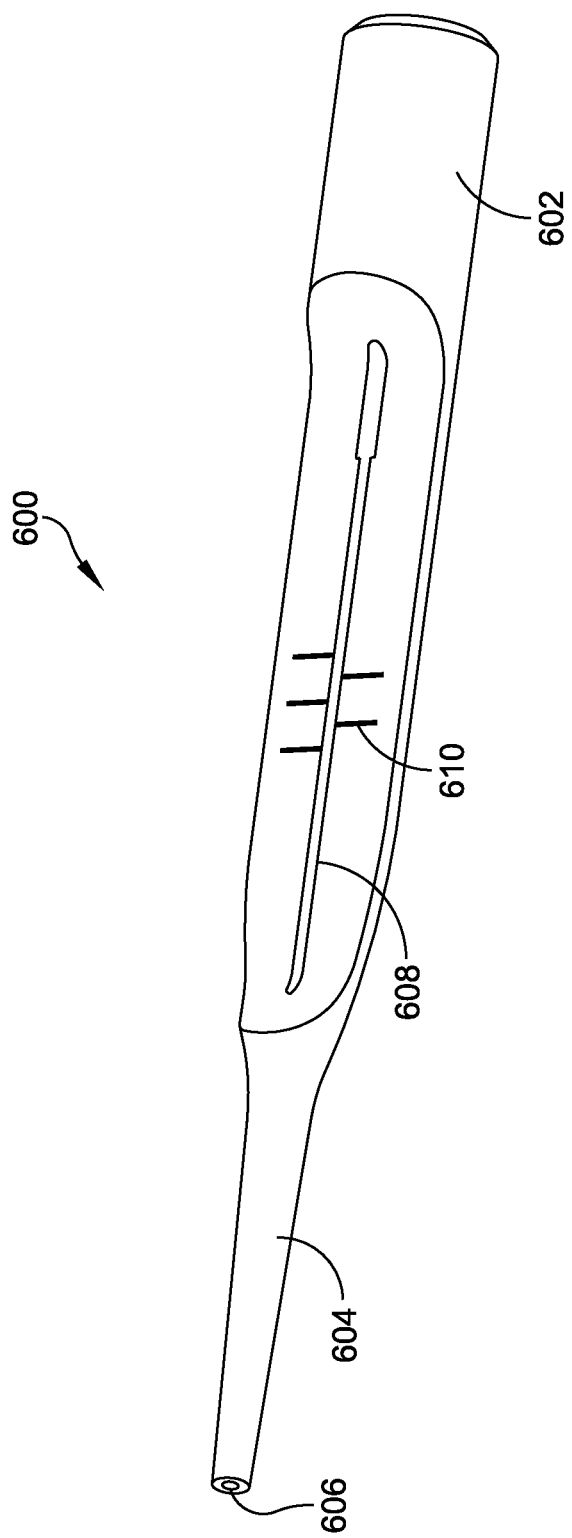
FIG. 17 illustrates a depth gauge, in accordance with some embodiments.

FIG. 17 illustrates a depth gauge 600 configured to provide a depth measurement corresponding to a length of a fixation screw required during a surgical procedure, as discussed in greater detail below. The depth gauge 600 includes a body 602 having a distal nose 604. The distal nose 604 defines an opening sized and configured to receive a k-wire (or other guide element) therethrough. The k-wire extends into a slot 608 defined in the body 602. A plurality of depth markings 610 provide a depth indication corresponding to the length of a fixation screw required during a surgical procedure.

FIGS. 18-35 illustrate various steps of a method of performing a lapidus surgical technique using the instruments illustrated in FIGS. 1-17, in accordance with some embodiments. In various embodiments, a medial incision is made in the first metatarsophalangeal (MT) joint. The medial first MT is exposed. A separate incision can be made to release the sesamoid first MT ligament to free up the sesamoids. In some embodiments, the medial eminence is not removed until correct alignment of the first metatarsal is achieved.

In some embodiments, a dorsomedial approach is planned to the proximal first TMT, for example, just medial to the EHL tendon. The approach can extend 2-2.5 cm on either side of the TMT. A skin incision is created while identifying and protecting any overlying neurovascular structures. The incision may be deepened through the fascial layers to the dorsal capsule of the TMT. Blunt dissection may be used to release the EHL off the TMT and retract the tendon laterally. The location of the first TMT joint may be confirmed either directly or using fluoroscopy. In some embodiments, a capsulotomy of the first TMT is performed to expose the entire joint, including complete exposure of the plantar and lateral aspects of the joint.

Figure 18:
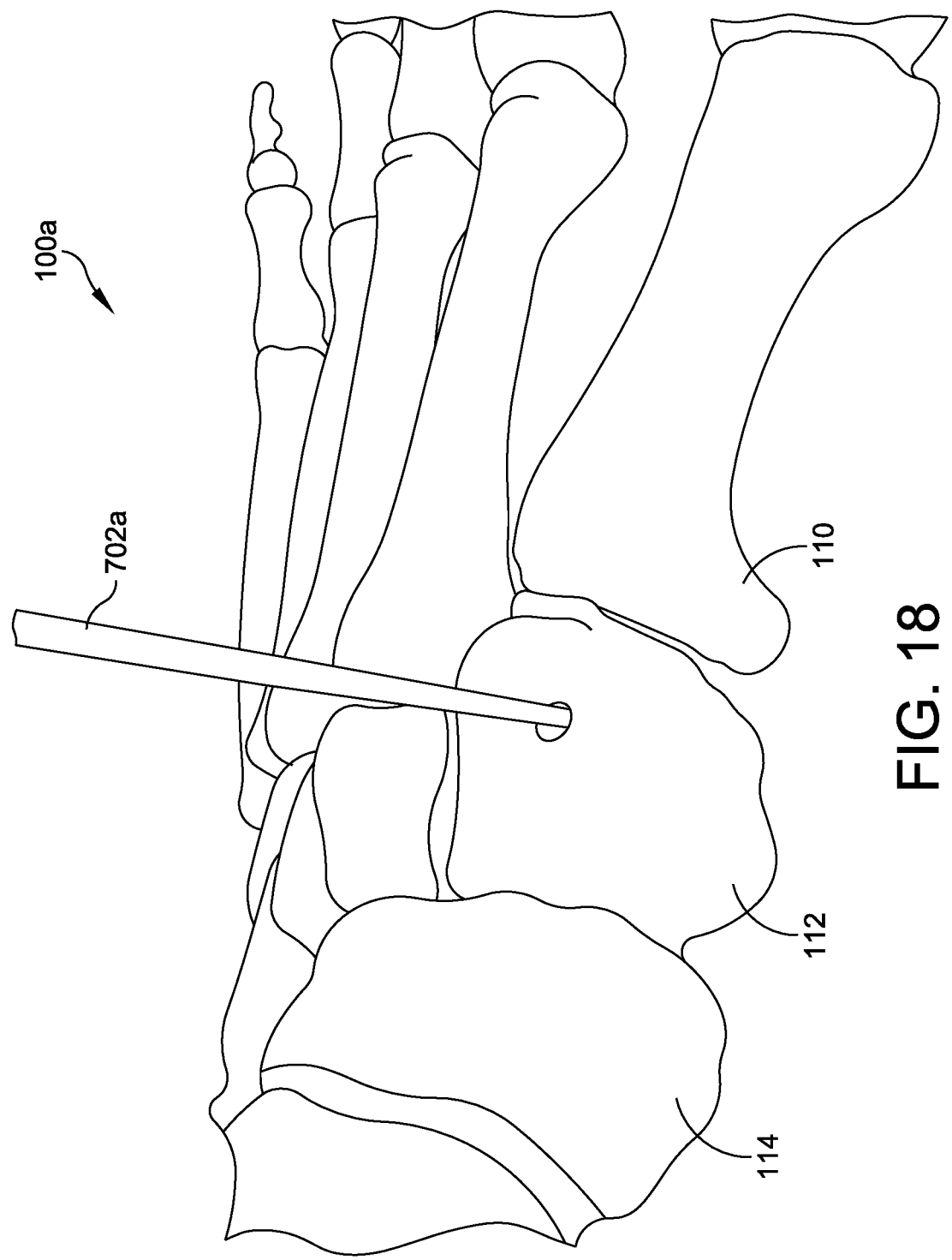
FIG. 18 illustrates a first pin inserted into a first metatarsal, in accordance with some embodiments.
Figure 19:
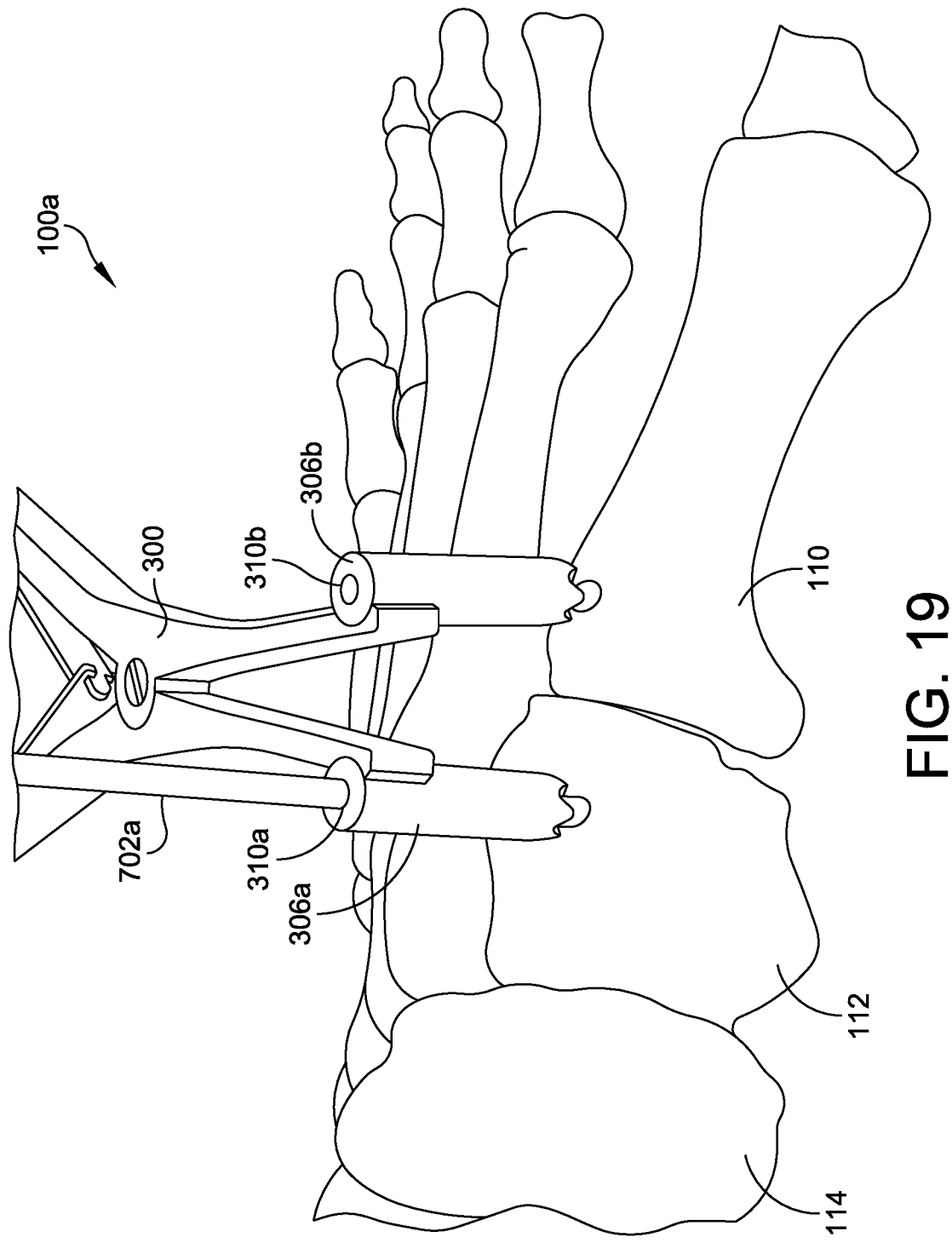
FIG. 19 illustrates a distractor coupled to the first pin, in accordance with some embodiments.
Figure 20:
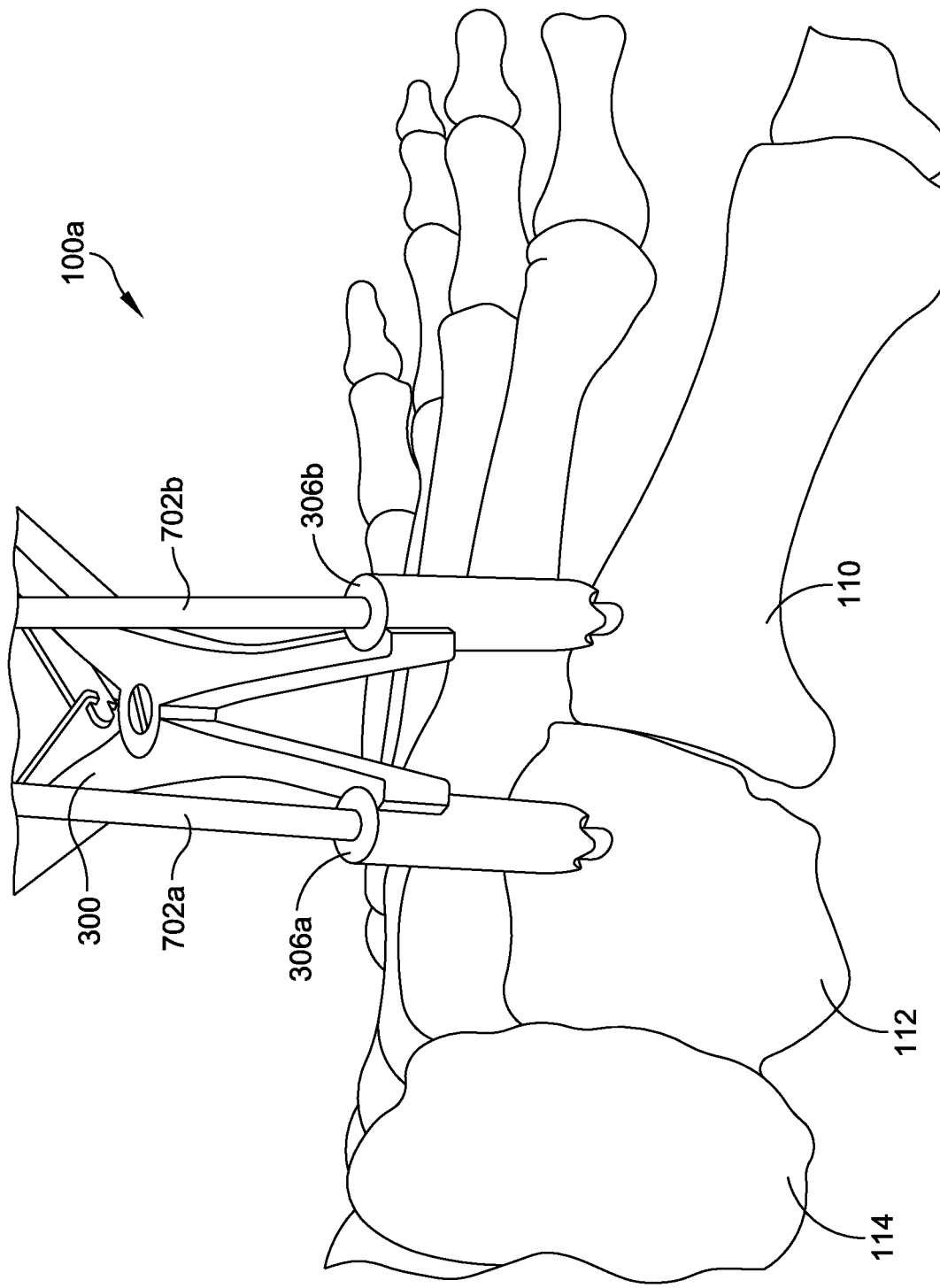
FIG. 20 illustrates a second pin inserted through a second opening of the distractor and into a medial cuneiform, in accordance with some embodiments.
Figure 21:
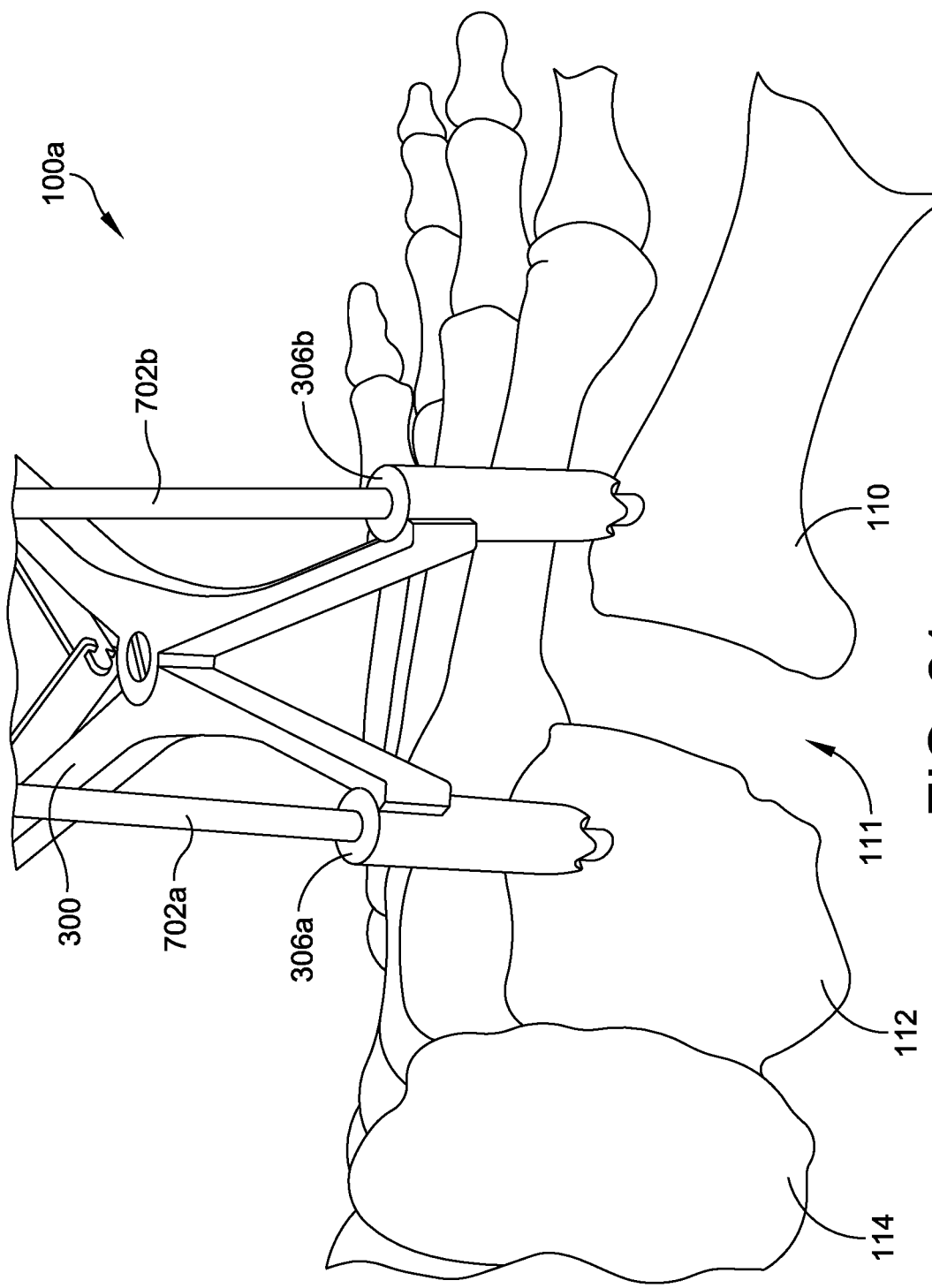
FIG. 21 illustrates a distracted joint formed by operation of the distractor, in accordance with some embodiments.
Figure 22:
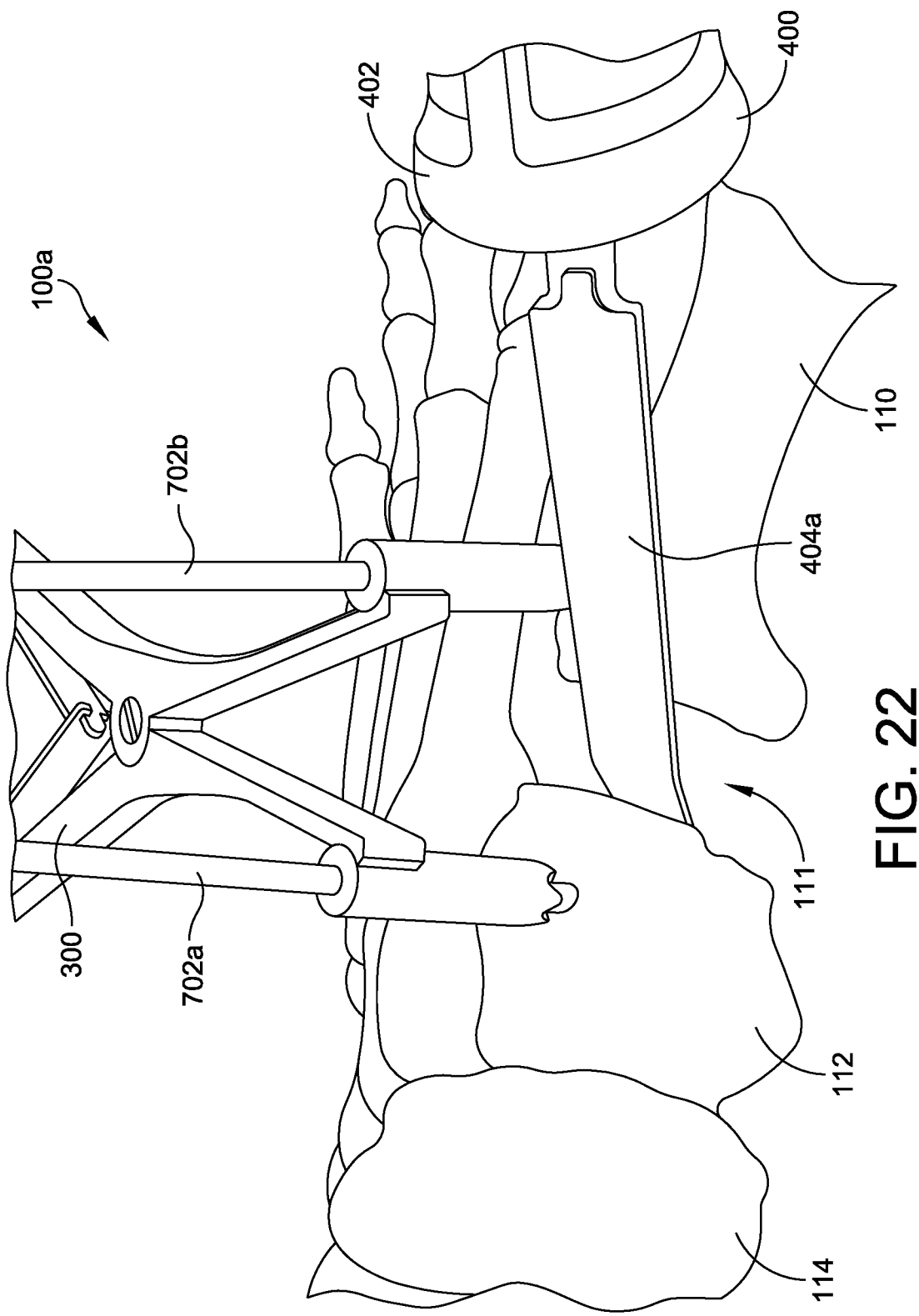
FIG. 22 illustrates removal of cartilage from the distracted joint of FIG. 21, in accordance with some embodiments.
Figure 23:
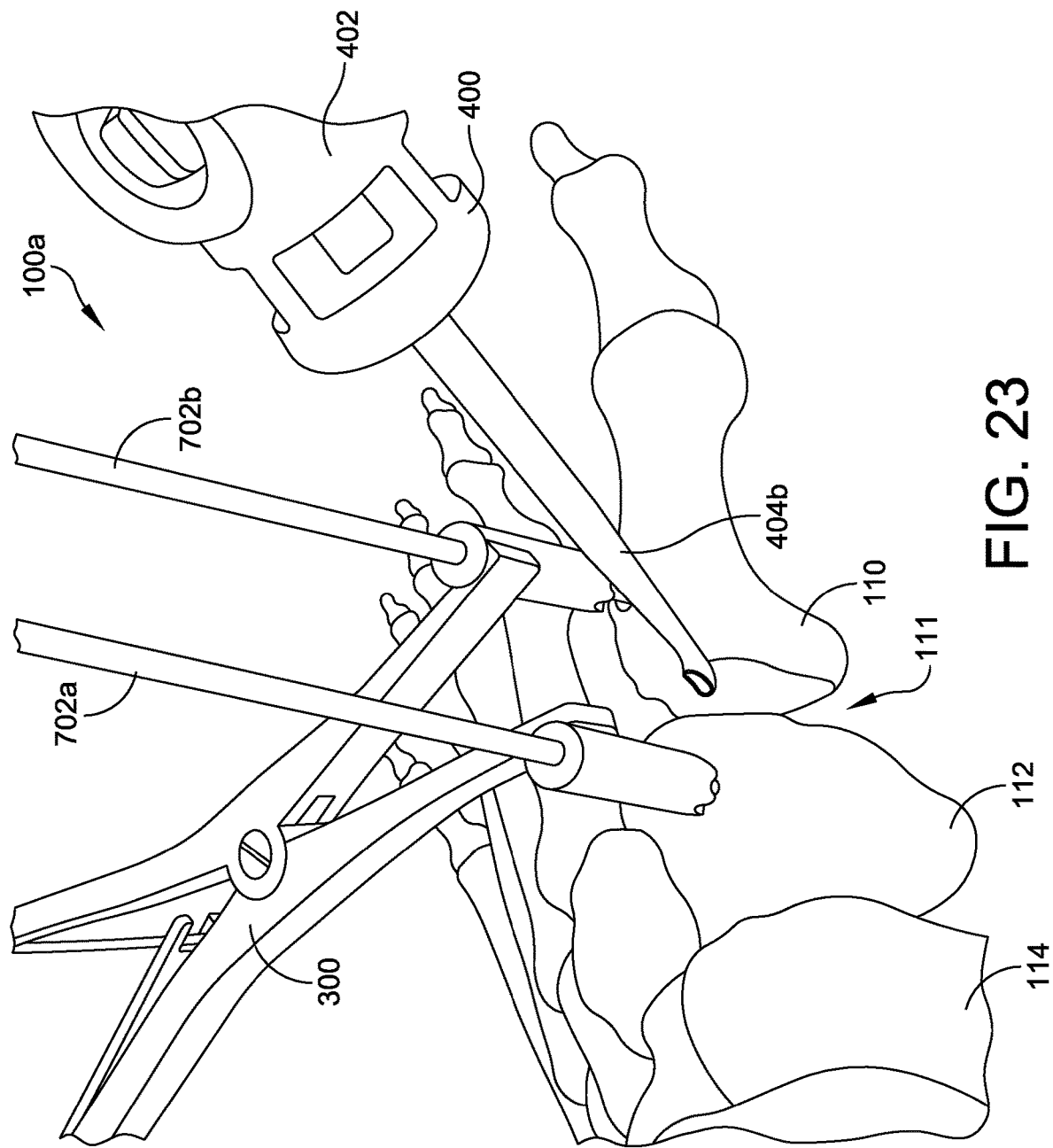
FIG. 23 illustrates formation of multiple holes in adjacent surfaces of the joint of FIG. 22, in accordance with some embodiments.
Figure 24:
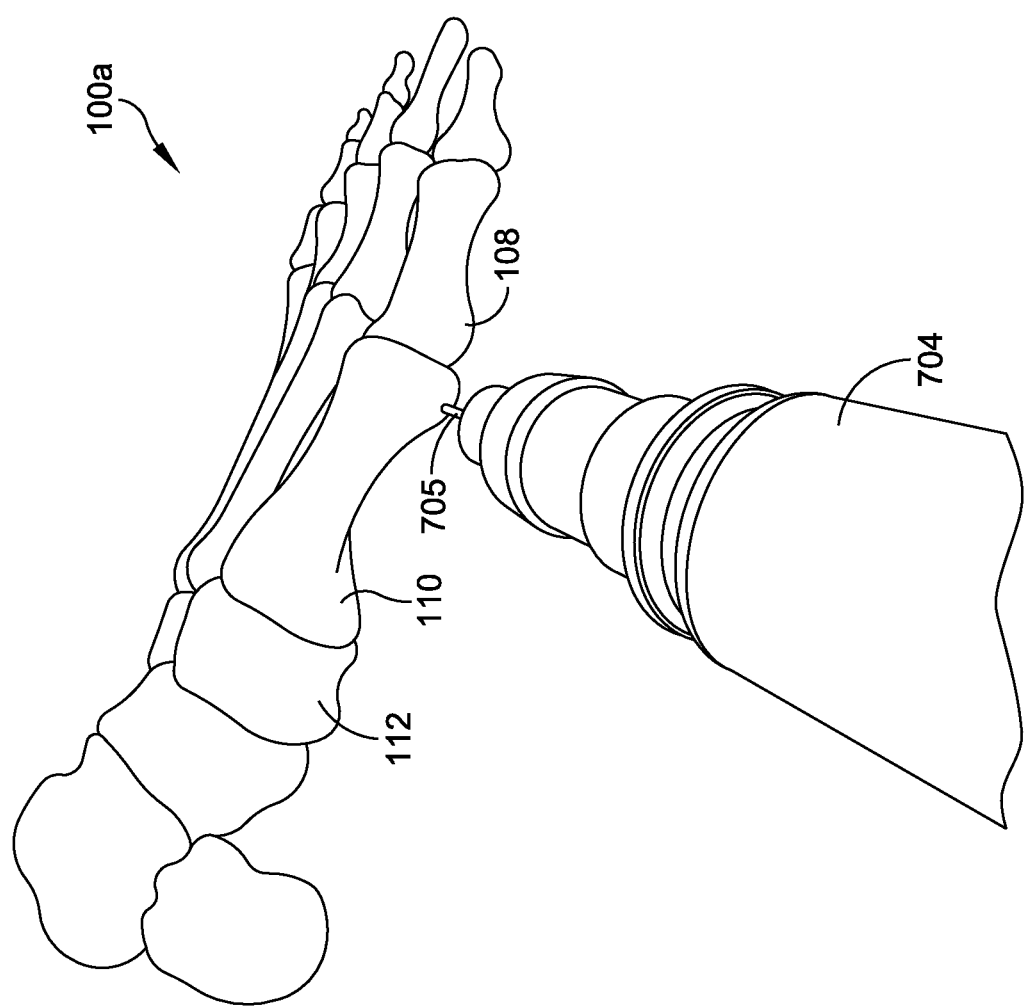
FIG. 24 illustrates formation of a hole through a first bone after the first joint of FIG. 23 has been reduced, in accordance with some embodiments.
Figure 25:
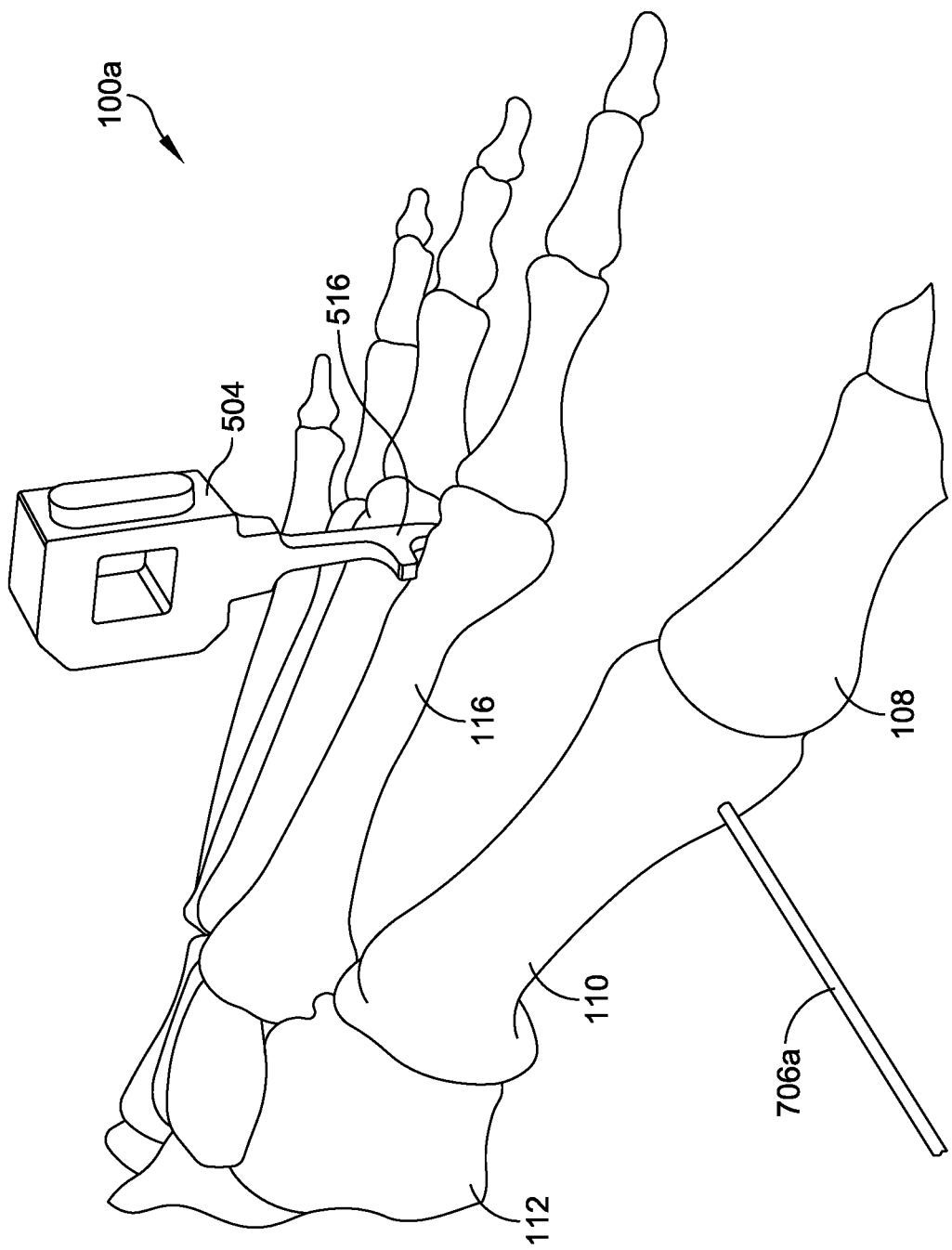
FIG. 25 illustrates a hook portion of a clamp positioned adjacent to a second metatarsal, in accordance with some embodiments.
Figure 26:
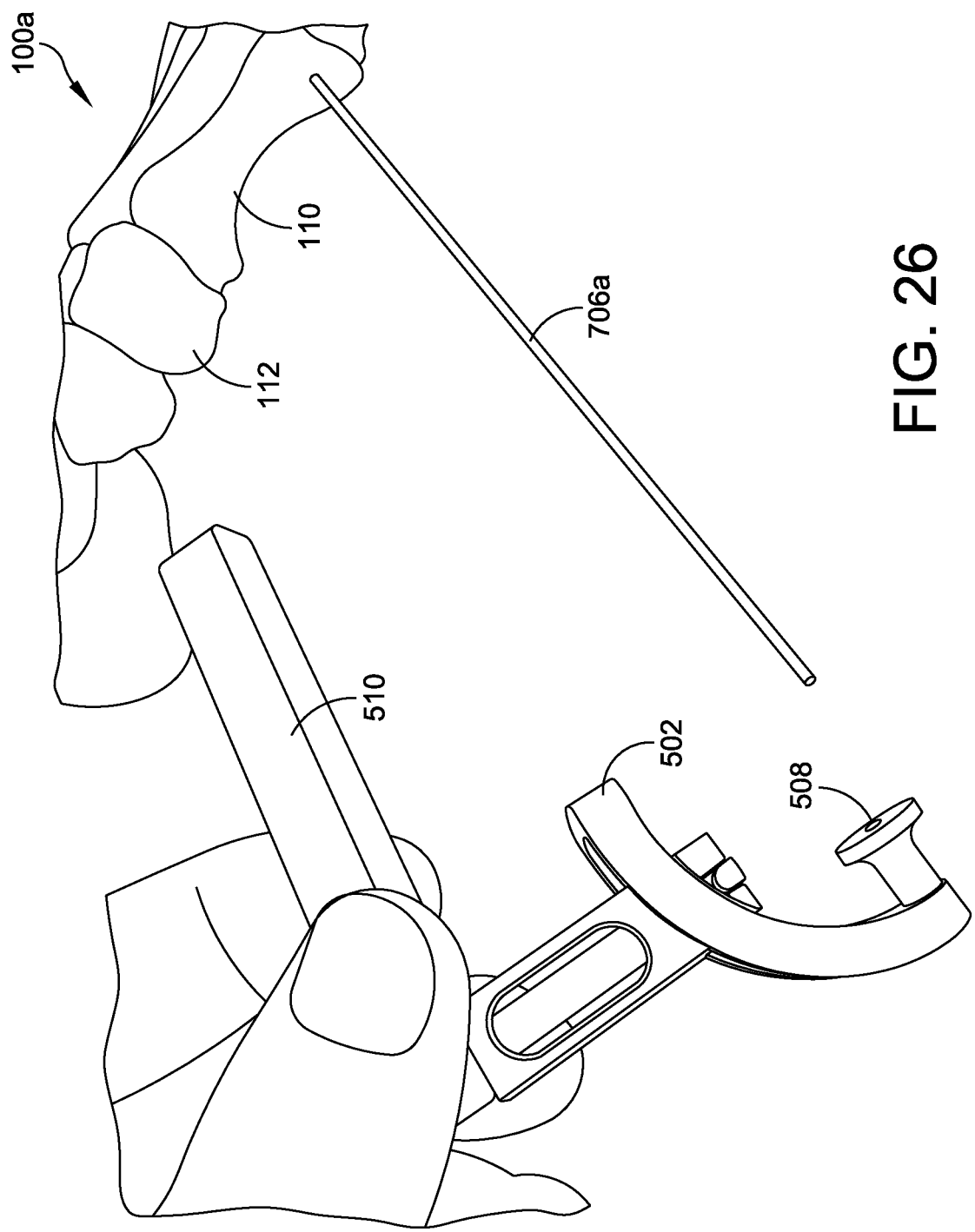
FIG. 26 illustrates a ratcheting barrel portion of a clamp positioned adjacent to a first k-wire coupled to the first metatarsal, in accordance with some embodiments.
Figure 27:
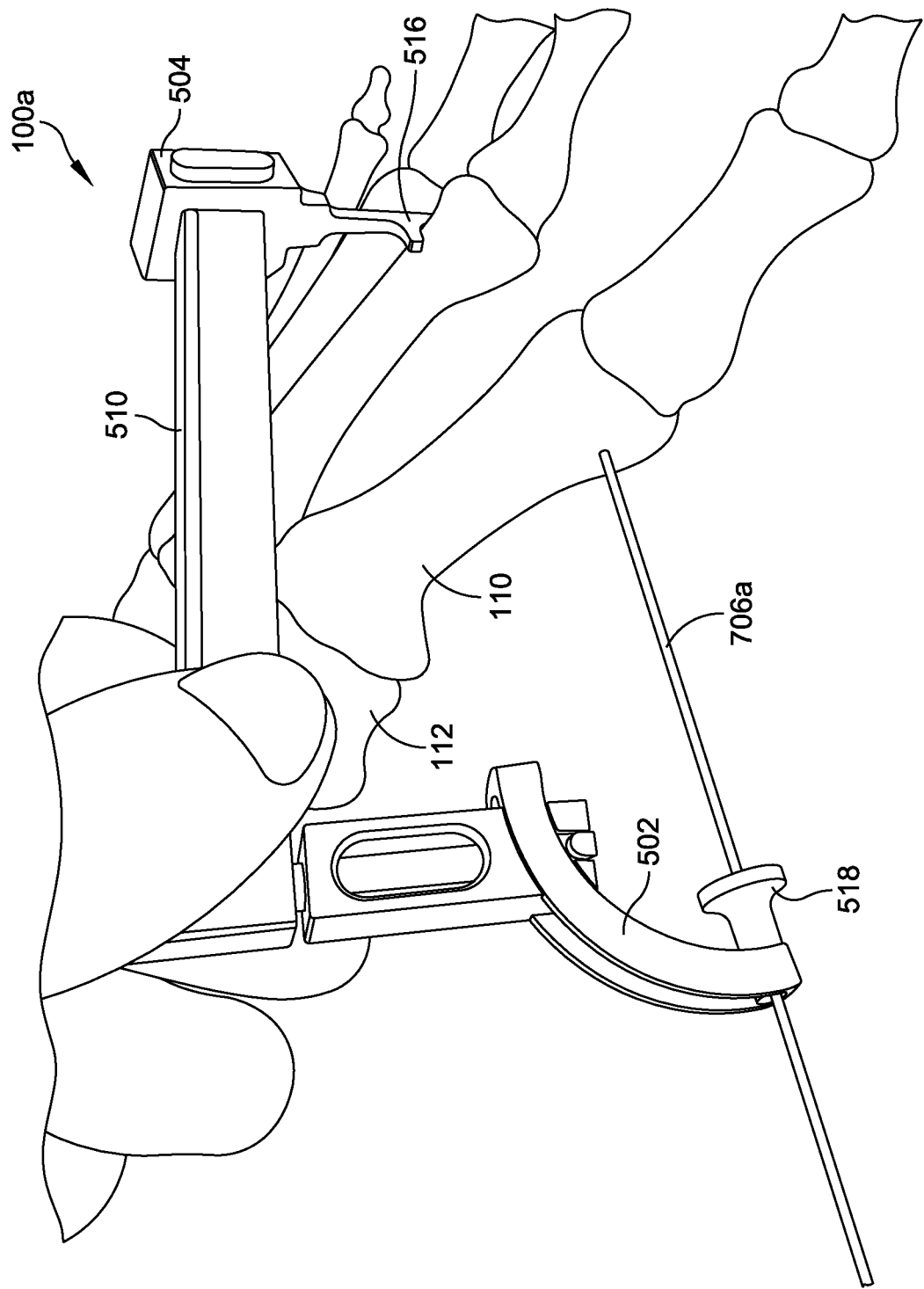
FIG. 27 illustrates the ratcheting barrel portion of the clamp slideably positioned over the first k-wire, in accordance with some embodiments.
Figure 28:
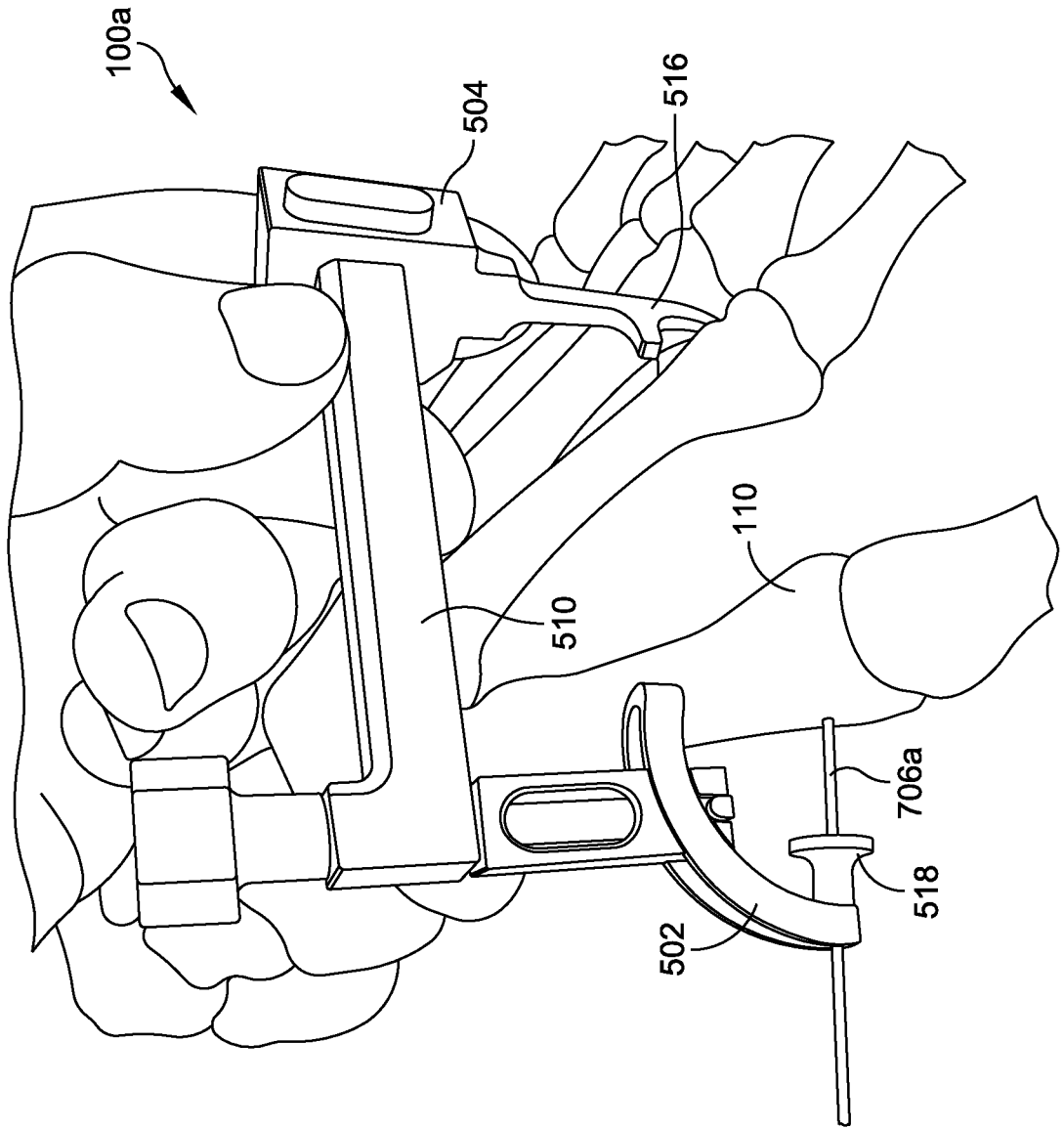
FIG. 28 illustrates the hook portion of the clamp coupled to the ratcheting barrel portion of the clamp, in accordance with some embodiments.
Figure 29:
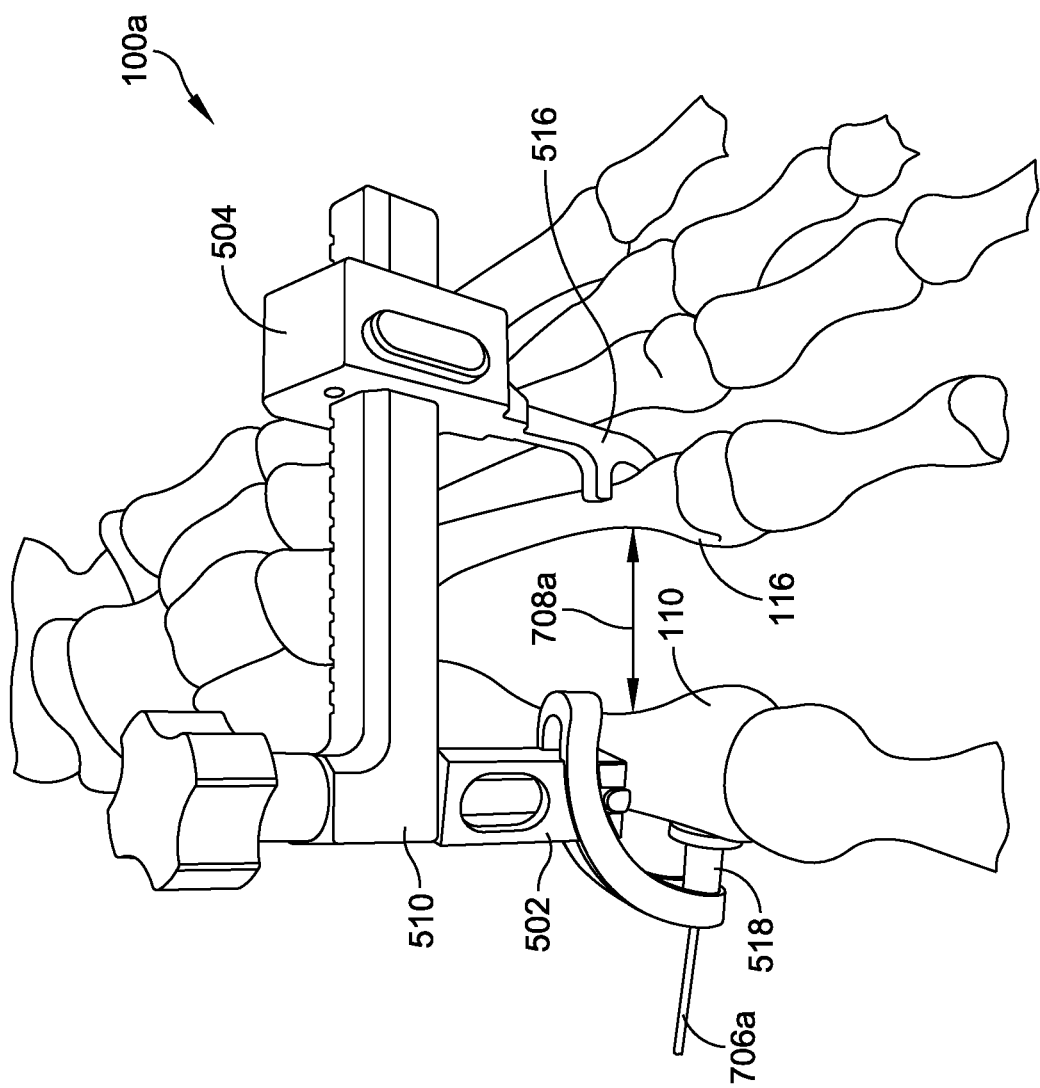
FIG. 29 illustrates the clamp of FIG. 28 in a partially clamped position, in accordance with some embodiments.
Figure 30:
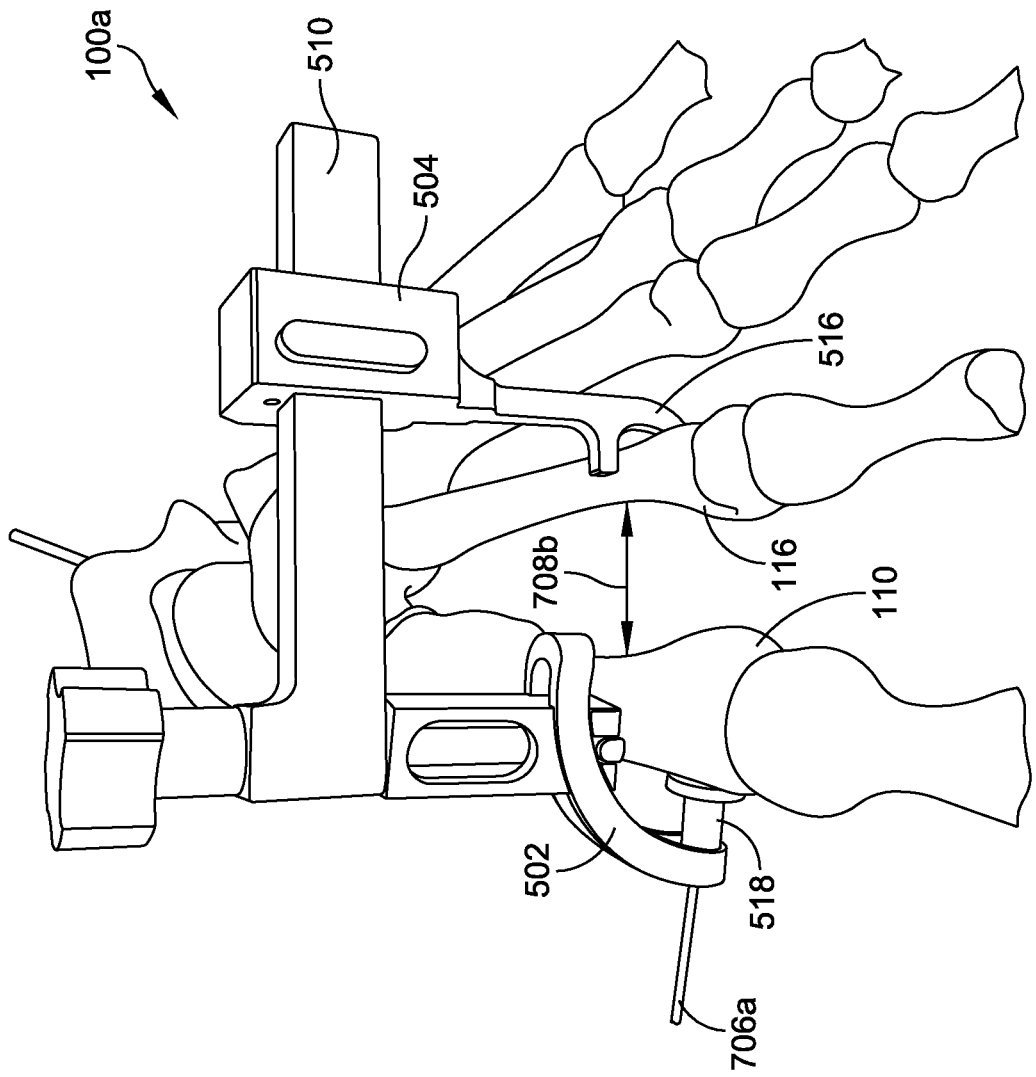
FIG. 30 illustrates the clamp of FIG. 28 in a fully clamped position, in accordance with some embodiments.

FIGS. 18-23 illustrate various steps of preparing a TMT joint, in accordance with some embodiments. As illustrated in FIG. 18, a first pin or wire 702a, such as a threaded Steinmann pin, is inserted into a bone at a surgical site 100, such as the medial cuneiform 112, at a predetermined position, such as, for example, approximately 4 mm proximal to the TMT joint. To ensure all inserted pins are parallel, and as illustrated in FIG. 19, a distractor 300 is coupled to the first pin 702 in the medial cuneiform by sliding the first pin 702 through a first opening 310a formed in a first head 306a of the distractor 300. The distractor 300 is opened to a desired position over the base of the first metatarsal 110 at a predetermined position, such as, for example, approximately 4 mm distal to the TMT joint. A second pin 702b, such as a second threaded Steinmann pin, is inserted through a second hole 310b or wire guide formed through a second head 306b of the distractor and into the base of the first metatarsal 114.

In some embodiments, after inserting the first and second pins 702a, 702b, the distractor 300 is actuated to distract the joint 111 to a predetermined distance, such as, for example, approximately 10 mm to 15 mm. In some embodiments, one or more tools included in a joint preparation kit 400 (FIG. 15) may be used to prepare the distracted joint 111. For example, in some embodiments, macro joint preparation may include use of a osteotome 404b, 404c and disposable handle 402 to remove articular cartilage in its entirety from the TMT joint. In some embodiments, cartilage is removed completely from the joint's plantar lateral aspect. As another example, in some embodiments, micro joint preparation includes use of a straight or bent curette 404a with a disposable handle to remove any remaining cartilage, while minimizing first metatarsal shortening.

In some embodiments, the first TMT joint is "feathered," for example, using an osteotome 404b, 404c, to increase the bony surfaces. Multiple small holes may be formed to perforate the subchondral plate on both adjoining surfaces, for example, using a drill or other suitable instrument. The first metatarsal may be reduced such that it is parallel with the second metatarsal and to close the intermetatarsal (IM) angle.

FIGS. 24-32 illustrate various steps of reduction and alignment of the TMT joint, in accordance with some embodiments. In some embodiments, a k-wire 706a is inserted targeting the center of the first metatarsal head 110 such that the axis of the k-wire 706a is perpendicular to the first metatarsal shaft (see FIG. 24). A drill 704 or other instrument, in conjunction with a drill bit 705, burr, etc., may be used to form a hole in the first metatarsal 110 sized and configured to receive the k-wire 706a.

In some embodiments, a hook portion 504 of a clamp 500 is configured and used to capture the second metatarsal head 116 (see FIG. 25) through the incision previously made for the lateral soft tissue release and/or a stab incision if a lateral incision was not made. In some embodiments, the hook 516 is inserted into the incision at an angle to push it over the top of the second metatarsal 116.

In some embodiments, the clamp 500 includes a rotational member 520 coupled to and/or formed integrally with a ratcheting barrel portion 502. The ratcheting barrel portion 502 of the clamp 500 is slideably coupled to k-wire 706a previously inserted through the head of the first metatarsal 110 (see FIGS. 26-27). The ratcheting element 510 of the clamp 500 is coupled to the hook portion 504 and the distance between the ratcheting barrel portion 502 and the hook portion 504 is reduced from a first angle 708a until the desired IM angle 708b is achieved (see FIGS. 28-30).

Figure 31:
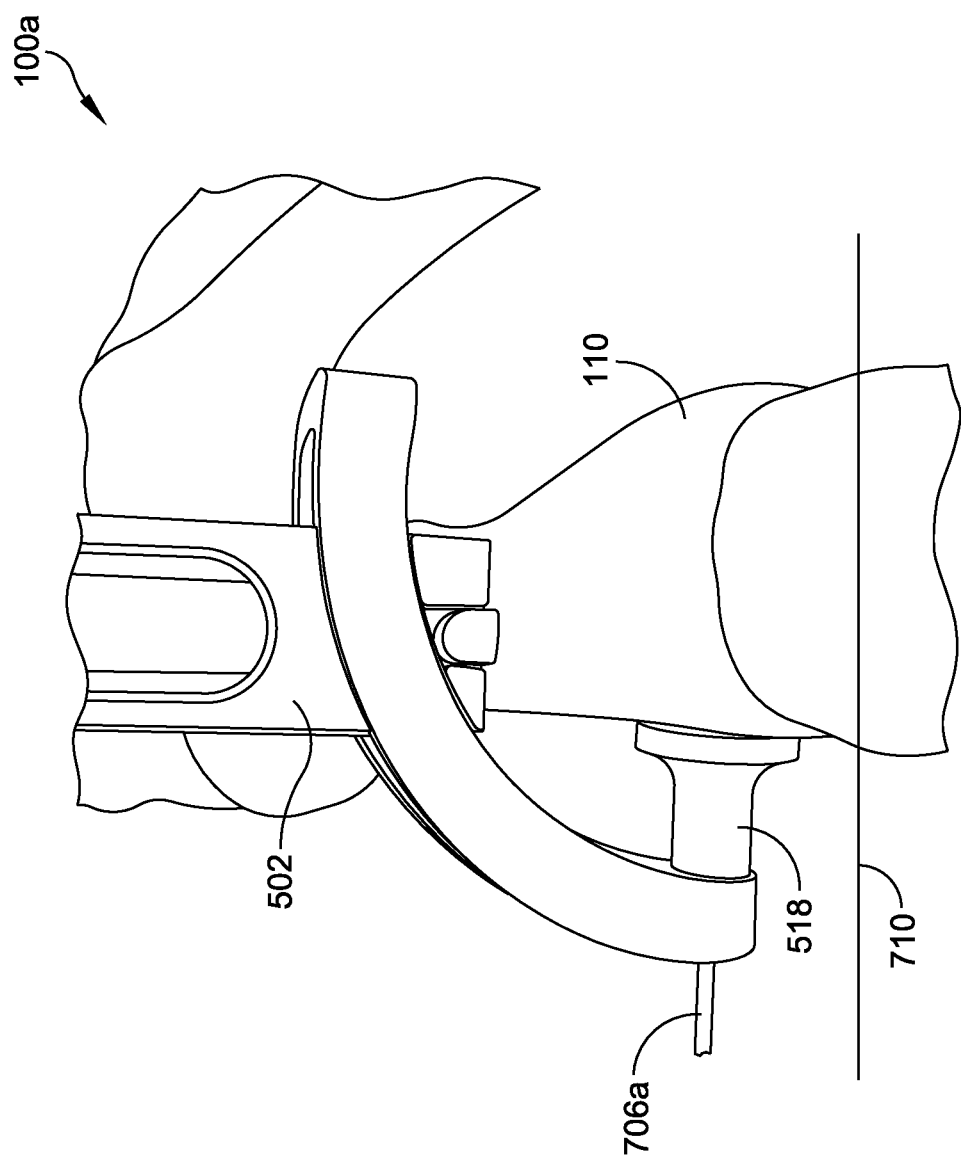
FIG. 31 illustrates a rotating member coupled of the ratcheting barrel portion of the clamp in a first position, in accordance with some embodiments.
Figure 32:
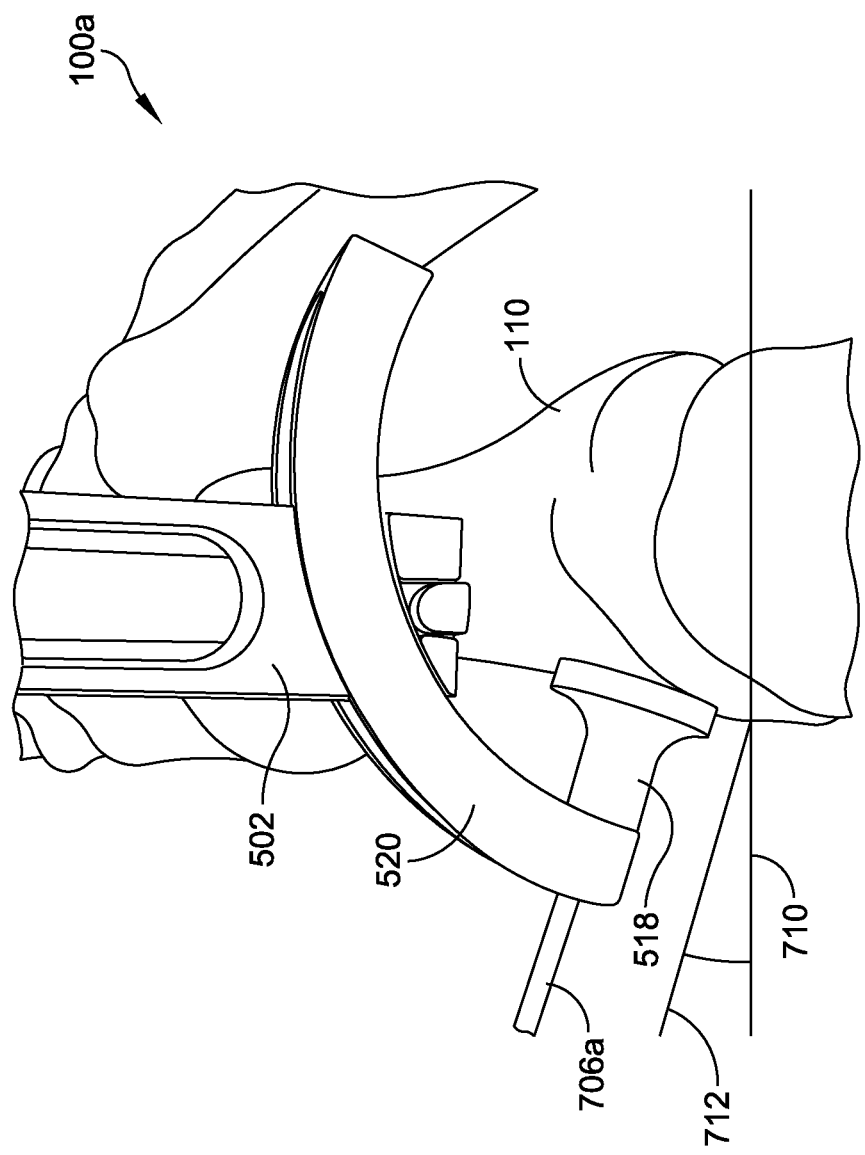
FIG. 32 illustrates the rotating member of the ratcheting barrel portion in a second position, in accordance with some embodiments.

In addition to reducing the distance between the ratcheting barrel portion 502 and the hook portion 504 to achieve the desired IM angle 708b, the rotating member 520 of the ratcheting barrel portion 502 is configured to rotate the first metatarsal 110 (in the frontal plane) until the sesamoids are positioned at a predetermined location under the metatarsal head (see FIGS. 31-32). Rotation of the first metatarsal 110 may occur simultaneously and/or sequentially with reduction of the distance between the ratcheting barrel portion 502 and the hook portion 504. The first metatarsal 110 may be rotated from a first angle 708 to a second angle 710.

Figure 33:
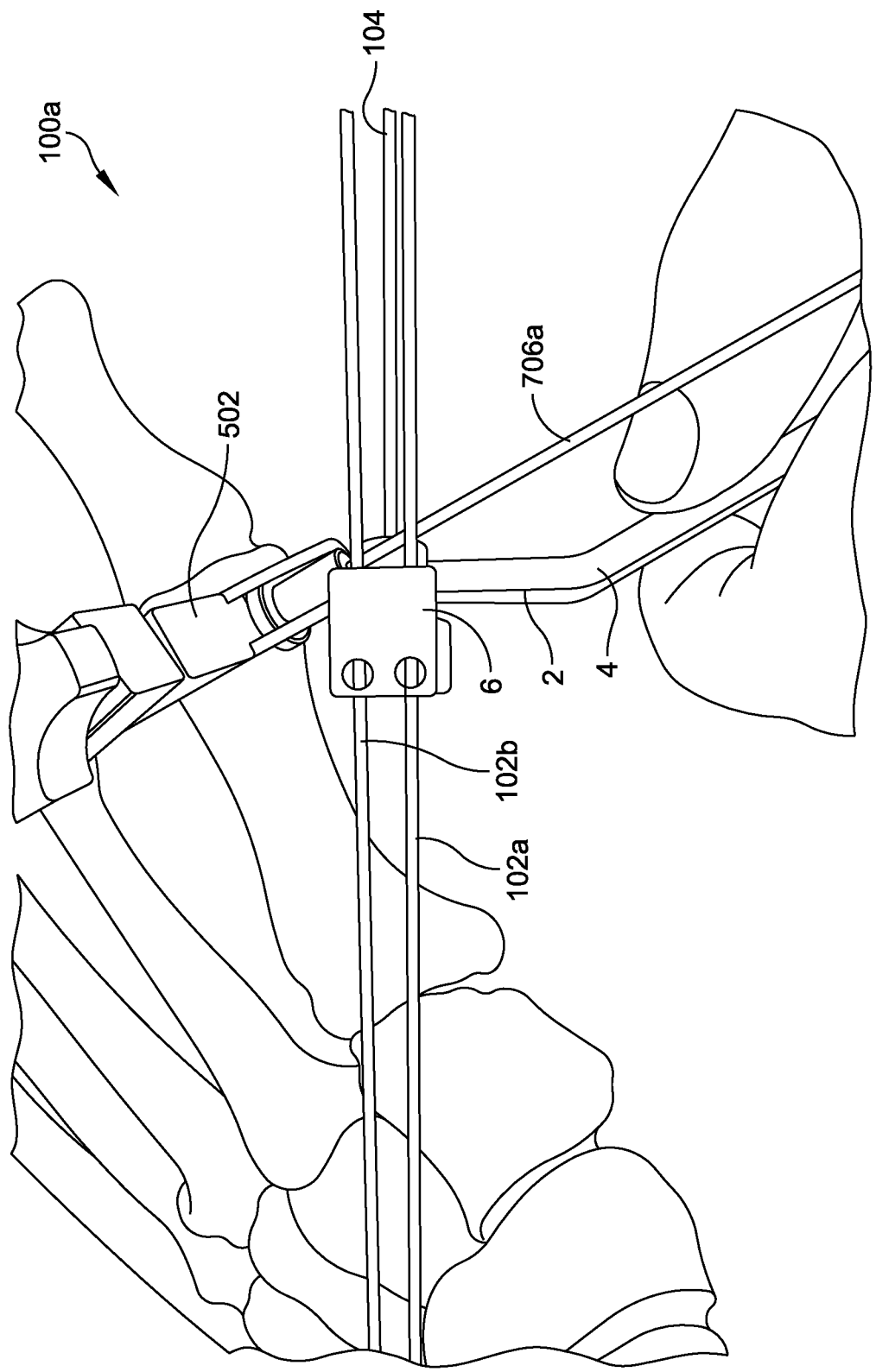
FIG. 33 illustrates a surgical targeting guide positioned adjacent to the first metatarsal to provide insertion of a second k-wire into the first metatarsal, medial cuneiform, and intermediate cuneiform, in accordance with some embodiments.
Figure 34:
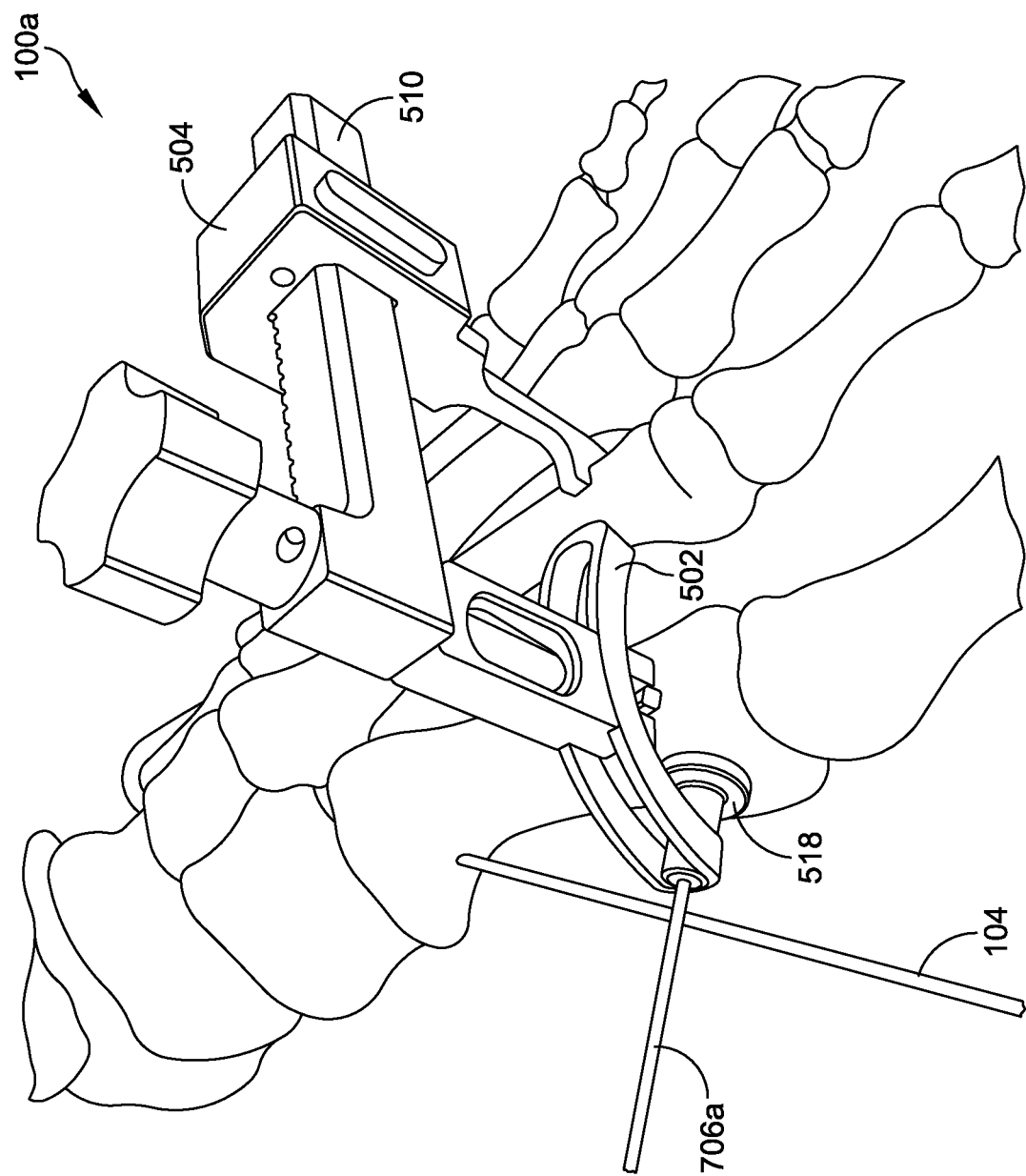
FIG. 34 illustrates the surgical site of FIG. 33 after insertion of the second k-wire, in accordance with some embodiments.

FIGS. 33-34 illustrate various steps of interfragmentary fastener placement, in accordance with some embodiments. A surgical targeting guide, such as any of the surgical targeting guides 2-2e described and illustrated in conjunction with FIGS. 1-11, is configured to position a guide element for a fastener. As discussed above, a first guide pin 102a and a second guide pin 102b are inserted into the guide holes 64a, 64b defined by a targeting tower 6. The surgical targeting guide 2 is positioned at the desired entry point and, in an optional step, an appropriate targeting guide pin 24e_1, 24e_2 may be selected. In some embodiments, the guide pins 102a, 102b are viewed under fluoroscopy to confirm targeting of the center of the middle cuneiform 114. Fluoroscopy may also be used to ensure that the surgical targeting guide 2 is straight by aligning a tip 27 of the targeting shaft 26 between the two guide pins 102a, 102b. Aligning the tip 27 of the targeting shaft 26 between the two guide pins 102a, 102b ensures that the desired trajectory is achieved. With the correct alignment confirmed, a fastener guide wire, e.g. k-wire 104, is driven into the intermediate cuneiform 116.

In some embodiments, the surgical targeting guide 2 is removed from the surgical site and a depth gauge 600 (see FIG. 17) is used to measure a fastener length required. A pilot hole may be prepared using a drill 704 and the k-wire 104. Using the k-wire 104 as a guide, a suitable fastener, such as a 4.0 mm screw, is placed across the 1st TMC fusion site and into the intermediate cuneiform 116 using any suitable drive, such as a driver and ratcheting handle. In some embodiments, additional compression of the TMC fusion site may be achieved through the compression slot features on a bone plate coupled to the site, as described in greater detail below.

Figure 35:
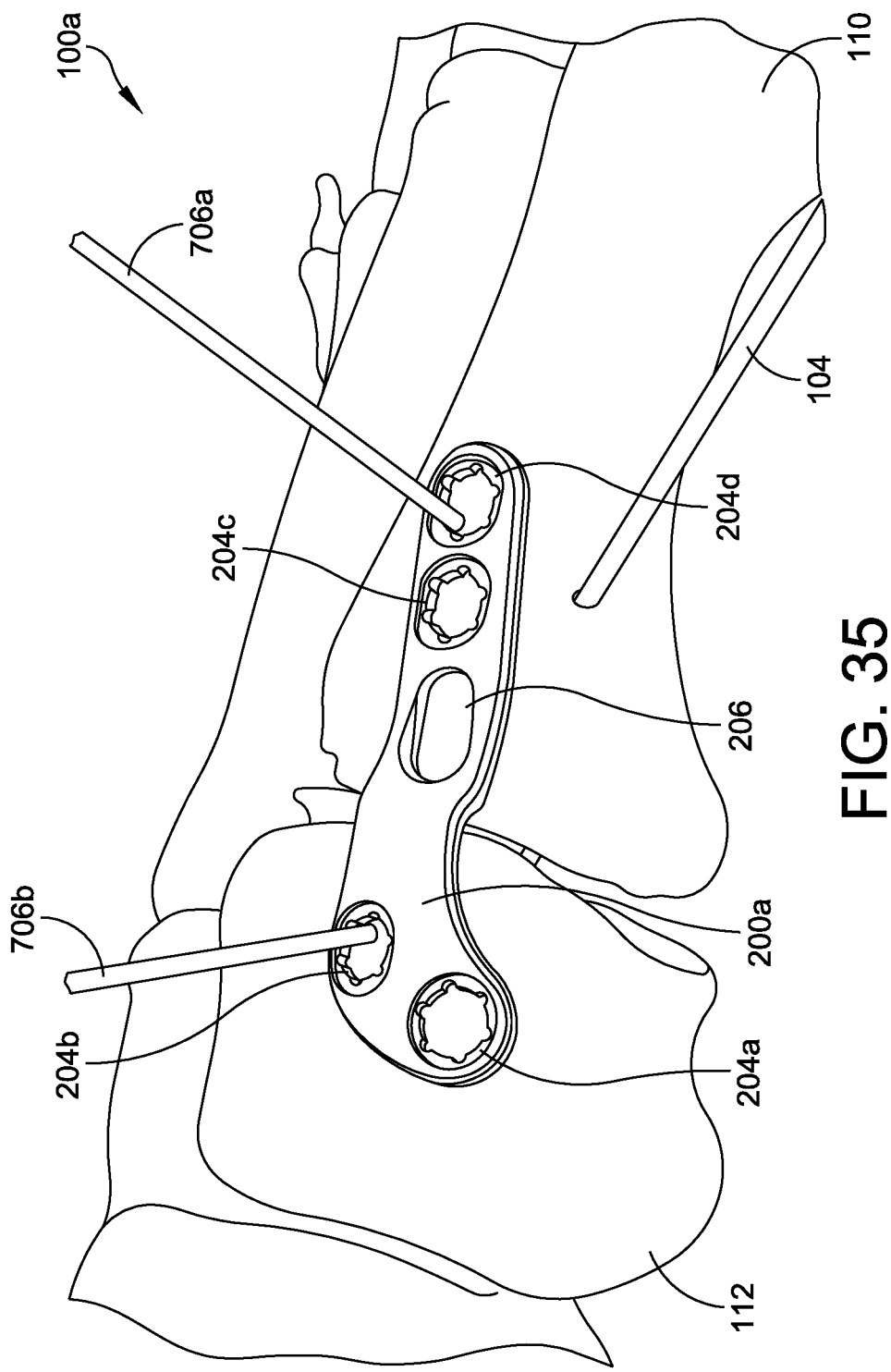
FIG. 35 illustrates the surgical site of FIG. 3 having the clamp removed therefrom and a bone plate coupled to the first metatarsal and the medial cuneiform and extending over the joint defined therebetween, in accordance with some embodiments.
Figure 36:
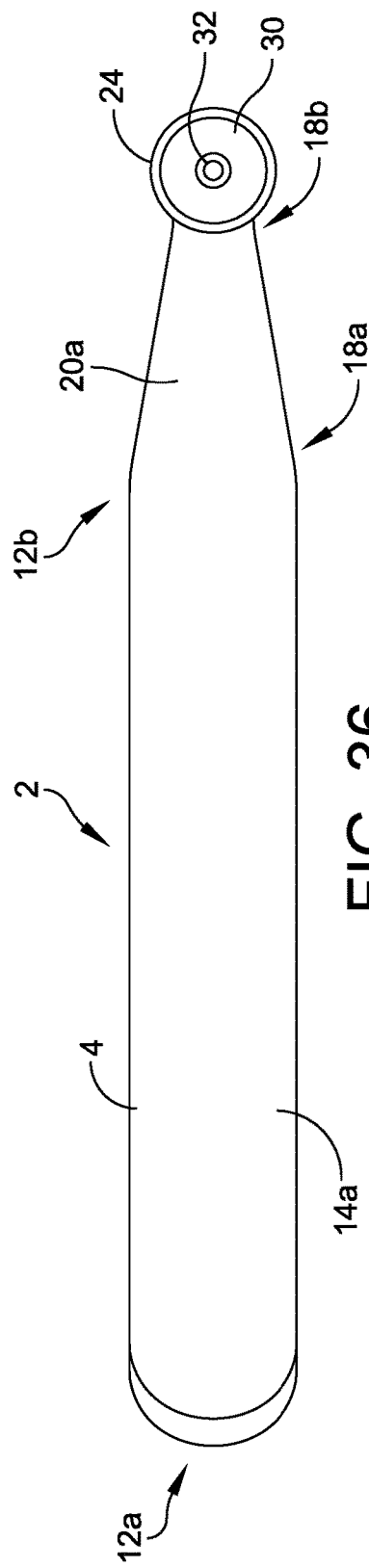
FIG. 36 illustrates a surgical targeting guide including a targeting guide handle, in accordance with some embodiments.

FIG. 35 illustrates a bone plate 200a coupled to the TMC fusion site, in accordance with some embodiments. In various embodiments, a suitable bone plate 200a may be selected from multiple options and designs, such as, for example, the bone plates 200a, 200b illustrated in FIGS. 12-13. In some embodiments, the bone plates 200a are left/right specific and/or have plantar steps to maintain an anatomical fit across the 1st TMT joint. In some embodiments, the plantar steps have a smooth dorsal transition to prevent soft tissue irritation. In some embodiments, a bone plate 200b includes a medial out of plane locking screw hole for placement of a screw from the first metatarsal to the second metatarsal for additional stability.

In some embodiments, a bone plate 200a is placed dorso-medial over the first TMT joint such that the compression slot is distal to the joint and completely clears the joint space. In some embodiments, provisional fixation of a bone plate 200a may be achieved by placing one or more temporary fixation pins 706a, 706b proximal and/or distal to the joint in any plate fastener hole 204a-204d. In some embodiments, the bone plate 200a includes one or more locking fastener holes 204a-204d configured to receive on-axis and/or angled fasteners therein. When using a locking fastener on-axis with the bone plate 200a, a locking drill guide may be threaded into the locking hole 204a-204d and a drill may be inserted through the locking drill guide to an appropriate depth, for example, as determined by use of a depth gauge. A fastener, such as a locking and/or non-locking fastener may be inserted through one or more of the fastener holes 204a-204d defined by the bone plate.

In some embodiments, proximal temporary fixation pins are removed from additional fastener holes 204a-204d in the plate and locking and/or non-locking fasteners are inserted through the additional fastener holes 204a-204d. Once proximal fixation is achieved, a hole may be drilled at the furthest distal point on the compression slot 206. A non-locking fastener may be inserted through the compression slot 206 until fully seated into the bone plate 202a. Compression across the fusion site is created as the fastener travels to the center of the compression slot 206. Additional fasteners, such as locking and/or non-locking fasteners, may be inserted into fastener holes defined by the bone plate 200a on a second side of the joint to fix the compression created by the non-locking fastener inserted through the slot.

In some embodiments, one or more locking and/or non-locking fasteners provide polyaxial locking capabilities. To engage a locking screw off-axis to the plate threads, a polyaxial drill guide may be placed into the desired locking hole 204a-204d to provide a pilot hole formed at an angle with respect to a central axis of the fastener hole 204a-204d.

Although the subject matter has been described in terms of exemplary embodiments, it is not limited thereto. Rather, the appended claims should be construed broadly, to include other variants and embodiments, which may be made by those skilled in the art.

What is claimed is:

1. A method for using a targeting guide, comprising:
positioning a targeting guide adjacent to a target site, the targeting guide comprising a handle defining a targeting hole and a targeting tower coupled to the handle, the targeting tower defining at least a first guide hole and a second guide hole;
inserting a first guide pin through the first guide hole and a second guide pin through the second guide hole;
aligning the first guide pin and the second guide pin with one or more bone portions at the target site;
aligning the first guide pin and the second guide pin with the targeting hole; and
inserting a guide element through the targeting hole into at least a first bone portion and a second bone portion at the target site; and
wherein an inner wall of the targeting tower defines an opening that includes two tabs that extend inwardly so as to be arranged in spaced-apart confronting relation.

2. The method of using a targeting guide claim 1, further comprising:
coupling the targeting tower to a targeting pin coupled to the handle prior to positioning a surgical guide adjacent to a surgical site.

3. The method of using the targeting guide of claim 1, wherein aligning the first guide pin and the second guide pin with the targeting hole comprises aligning a tip of a targeting pin between the first guide pin and the second guide pin.

4. A method for using a targeting guide, comprising:
providing a handle that defines a targeting hole;
coupling a targeting pin to the handle so that a portion of the targeting pin is located within the targeting hole;
inserting a k-wire into the targeting hole;
coupling a targeting tower to the handle, the targeting tower defining at least a first guide hole and a second guide hole each sized and configured to receive a respective guide pin configured to indicate alignment of the k-wire when inserted through the targeting hole; and
coupling the targeting tower to a targeting shaft of the targeting pin so that an inner wall of that defines a hole in the targeting tower receiving the targeting shaft includes two tabs that extend inwardly so as to be arranged in spaced-apart confronting relation to thereby provide a preferred orientation of the targeting pin.

5. The method for using a targeting guide according to claim 4 wherein the targeting pin comprises a head and the targeting shaft, wherein the targeting shaft extends at a non-zero angle.

6. The method for using a targeting guide according to claim 4 wherein the at least one guide hole is sized and configured to receive a guide sleeve.

7. The method for using a targeting guide according to claim 4 wherein the handle comprises a first handle portion and a second handle portion; and
coupling the second handle portion to a distal end of the first handle portion at a predetermined, non-zero angle.

8. The method for using a targeting guide according to claim 4 further comprising:
coupling the handle to the targeting tower by a slot formed on a first one of the handle or the targeting tower and a tab formed on a second one of the handle or the targeting tower.

9. The method for using a targeting guide according to claim 4 comprising coupling a soft tissue guard to the handle.

10. The method for using a targeting guide according to claim 9 wherein the soft tissue guard defines at least one hole sized and configured to receive the targeting pin.

11. A method for using a targeting guide, comprising:
providing a targeting guide including a handle defining a targeting hole and including a targeting pin configured to be coupled to the handle, wherein the targeting pin defines the targeting hole, and a targeting tower configured to be coupled to the handle, the targeting tower defining at least a first guide hole and a second guide hole, wherein each of the first and second guide holes are sized and configured to receive a respective first guide pin and second guide pin therethrough, and wherein the first and second guide pins are configured to indicate alignment of a k-wire inserted through the targeting hole defined by the handle, the targeting tower further including an opening sized and configured to slideably couple the targeting tower to a targeting shaft of the targeting pin, wherein an inner wall of the targeting tower that defines the opening includes two tabs that extend inwardly so as to be arranged in spaced-apart confronting relation to thereby provide a preferred orientation of the targeting pin;
positioning the targeting guide adjacent to a target site;
inserting a first guide pin through the first guide hole and a second guide pin through the second guide hole;
aligning the first guide pin and the second guide pin with one or more structures at the target site;
aligning the first guide pin and the second guide pin with the targeting hole; and
inserting a guide element through the targeting hole into at least a first bone portion and a second bone portion at the target site.

12. The method of using a targeting guide of claim 11, further comprising:
coupling the targeting tower to the targeting shaft of the targeting pin coupled to the handle prior to positioning a surgical guide adjacent to a surgical site.

13. The method of using the targeting guide of claim 11, wherein aligning the first guide pin and the second guide pin with the targeting hole comprises aligning a tip of the targeting shaft of the targeting pin defining the targeting hole between the first guide pin and the second guide pin.

14. The method for using a targeting guide according to claim 11 wherein the targeting pin comprises a head and the targeting shaft, wherein the targeting shaft extends at a non-zero angle.

15. The method for using a targeting guide according to claim 11 wherein the at least one guide hole is sized and configured to receive a guide sleeve.

16. The method for using a targeting guide according to claim 11 wherein the handle comprises a first handle portion and a second handle portion; and
coupling the second handle portion to a distal end of the first handle portion at a predetermined, non-zero angle.

17. The method for using a targeting guide according to claim 11 further comprising:
coupling the handle to the targeting tower by a slot formed on a first one of the handle or the targeting tower and a tab formed on a second one of the handle or the targeting tower.

18. The method for using a targeting guide according to claim 11 comprising coupling a soft tissue guard to the handle.

19. The method for using a targeting guide according to claim 18 wherein the soft tissue guard defines at least one hole sized and configured to receive the targeting pin.

* * * * *